(12) United States Patent
Heberlein et al.

(10) Patent No.: US 11,733,335 B2
(45) Date of Patent: Aug. 22, 2023

(54) METHOD FOR RECORDING DIAGNOSTIC MEASUREMENT DATA OF A HEAD OF AN EXAMINATION OBJECT IN HEAD IMAGING VIA A MAGNETIC RESONANCE DEVICE

(71) Applicants: Siemens Healthcare GmbH, Erlangen (DE); The General Hospital Corporation, Boston, MA (US)

(72) Inventors: Keith Aaron Heberlein, Charlestown, MA (US); Thomas Witzel, Boston, MA (US)

(73) Assignees: Siemens Healthcare GmbH, Erlangen (DE); The General Hospital Corporation, Boston, MA (US)

( * ) Notice: Subject to any disclaimer, the term of this patent is extended or adjusted under 35 U.S.C. 154(b) by 0 days.

(21) Appl. No.: 17/408,678

(22) Filed: Aug. 23, 2021

(65) Prior Publication Data
US 2022/0011390 A1    Jan. 13, 2022

Related U.S. Application Data

(63) Continuation of application No. 15/695,211, filed on Sep. 5, 2017, now Pat. No. 11,129,541, which is a
(Continued)

(51) Int. Cl.
*A61B 5/00* (2006.01)
*A61B 5/055* (2006.01)
(Continued)

(52) U.S. Cl.
CPC ........ *G01R 33/5601* (2013.01); *A61B 5/0042* (2013.01); *A61B 5/055* (2013.01); *G01R 33/5613* (2013.01)

(58) Field of Classification Search
CPC ............ G01R 33/5601; G01R 33/5613; G01R 33/5602; G01R 33/56341; G01R 33/543;
(Continued)

(56) References Cited

U.S. PATENT DOCUMENTS 5,341,292 A * 8/1994 Zamenhof ............ A61N 5/1031
                                                        600/509
5,488,297 A * 1/1996 Nakada ............ G01R 33/56341
                                                        324/309
(Continued)

FOREIGN PATENT DOCUMENTS

CN       1618399 A        5/2005
CN     101088023 A       12/2007
(Continued)

OTHER PUBLICATIONS

Haase et al (FLASH Imaging. Rapid NMR Imaging Using Low Flip-Angle Pulses Journal of Magnetic Resonance, vol. 67, pp. 258-266, 1986) (Year: 1986).*
(Continued)

*Primary Examiner* — Yi-Shan Yang
*Assistant Examiner* — Alexei Bykhovski
(74) *Attorney, Agent, or Firm* — Harness, Dickey & Pierce, P.L.C.

(57) ABSTRACT

A method is proposed for recording diagnostic measurement data of a head of an examination object in head imaging via a magnetic resonance device. The method comprises performing an overview scan of the head of the examination object, wherein overview measurement data is acquired in the overview scan and performing various diagnostic scans of the head of the examination object based on the acquired overview measurement data, wherein diagnostic measurement data is acquired in the various diagnostic scans.

19 Claims, 3 Drawing Sheets

Related U.S. Application Data continuation of application No. PCT/US2017/048345, filed on Aug. 24, 2017.

(60) Provisional application No. 62/424,570, filed on Nov. 21, 2016.

(51) Int. Cl.
  *G01R 33/56* (2006.01)
  *G01R 33/561* (2006.01)

(58) Field of Classification Search
  CPC ......... A61B 5/0042; A61B 5/055; A61B 5/74; A61B 5/0037
  See application file for complete search history.

(56) References Cited

U.S. PATENT DOCUMENTS

| | | | |
|---|---|---|---|
| 6,529,762 | B1 | 3/2003 | Ladebeck |
| 7,990,141 | B2 | 8/2011 | Wohlfarth |
| 8,190,232 | B2 | 5/2012 | Zhang et al. |
| 9,157,979 | B2 | 10/2015 | Miyazaki et al. |
| 2003/0042905 | A1 | 3/2003 | Miyazaki et al. |
| 2005/0110489 | A1 | 5/2005 | Miyoshi |
| 2006/0260050 | A1 | 11/2006 | Manzione |
| 2008/0197846 | A1 | 8/2008 | Zhai et al. |
| 2009/0069668 | A1 | 3/2009 | Stemmer |
| 2009/0093706 | A1* | 4/2009 | Zhang .............. A61B 5/417 382/128 |
| 2009/0289631 | A1 | 11/2009 | Van Den Brink et al. |
| 2010/0013475 | A1 | 1/2010 | Kimura |
| 2010/0261993 | A1 | 10/2010 | van der Kouwe et al. |
| 2011/0004092 | A1 | 1/2011 | Kato |
| 2012/0019247 | A1 | 1/2012 | Boernert et al. |
| 2012/0249498 | A1 | 10/2012 | Sugiyama et al. |
| 2013/0023754 | A1 | 1/2013 | Harder et al. |
| 2013/0204123 | A1 | 8/2013 | Feinberg |
| 2014/0009156 | A1 | 1/2014 | Doneva et al. |
| 2014/0210467 | A1* | 7/2014 | Hwang ............ G01R 33/56536 324/309 |
| 2015/0182117 | A1* | 7/2015 | Senegas ............... A61B 5/0037 600/410 |
| 2015/0282764 | A1 | 10/2015 | Greiser et al. |
| 2016/0058304 | A1 | 3/2016 | Emblem et al. |
| 2016/0132746 | A1 | 5/2016 | Saranathan et al. |
| 2016/0203599 | A1* | 7/2016 | Gillies ................ A61B 5/7271 382/132 |
| 2016/0228014 | A1* | 8/2016 | Witschey ........... A61B 5/02028 |

FOREIGN PATENT DOCUMENTS

| | | |
|---|---|---|
| CN | 101263399 A | 9/2008 |
| CN | 101627910 A | 1/2010 |
| CN | 101742963 A | 6/2010 |
| CN | 102525467 A | 7/2012 |
| CN | 103477238 A | 12/2013 |
| CN | 104970794 A | 10/2015 |
| DE | 102011079503 A1 | 1/2013 |

OTHER PUBLICATIONS

Akeson et al. Time-dependency in brain lesion enhancement with gadodiamide injection ACTA Radiologica, vol. 38, No. 1, pp. 19-24, 1997 (Year: 1997).*

Tsao (Ultrafast Imaging: Principles, Pitfalls, Solutions, and Applications Journal of Magnetic Resonance Imaging, vol. 32, pp. 252-266, 2010) (Year: 2010).*

Graif et al. Contrast-Enhanced MR Imaging of Malignant Brain Tumors AJNR: 6, pp. 855-862 (1985). (Year: 1985).*

International Search Report and Written Opinion dated Nov. 8, 2017.

International Preliminary Report on Patentability dated May 23, 2019.

Yanasak, Nathan E. et al.: "MR Imaging Artifacts and Parallel Imaging Techniques with Calibration Scanning: A New Twist on Old Problems"; in RadioGraphics; vol. 34; No. 2; pp. 532-549; Mar.-Apr. 2014.

Landis, Richard J. et al. "The Measurement of Observer Agreement for Categorical Data" Biometrics, vol. 33, No. 1, pp. 159-174, Mar. 1977.

Viera, Anthony J. et al. "Understanding interobserver agreement: the kappa statistic" Family Medicine, vol. 37, No. 5, pp. 360-363, May 2005.

Prakkamakul, Supada et al. "Ultrafast Brain MRI: Clinical Deployment and Comparison to Conventional Brain MRI at 3T" Journal of Neuroimaging, vol. 26, No. 5, pp. 503-510, Sep./Oct. 2016 // https://doi.org/10.1111/jon.12365.

Cohen, Mark S. et al. "Ultra-fast imaging" Magnetic Resonance Imaging, vol. 9, No. 1, pp. 1-37, 1991 // https://doi.org/10.1016/0730-725X(91)90094-3.

Griswold, Mark A. et al. "Basic Reconstruction Algorithms for Parallel Imaging" Part of the Medical Radiology book series (MEDRAD), Chapter Basic Reconstruction Algorithms for Parallel Imaging, 2007 // ISBN : 978-3-540-23102-8.

Tsao, Jeffrey "Ultrafast Imaging: Principles, Pitfalls, Solutions, and Applications" Journal of Magnetic Resonance Imaging, vol. 32, pp. 252-266, 2010.

Meshkar, A. et al. "Role of EPI-FLAIR in patients with acute stroke: a comparative analysis with FLAIR" American Journal of Neuroradiology, vol. 39, No. 5, pp. 878-883, May 2014.

Deshmane, Anagha et al. "Parallel MR imaging" Journal of Magnetic Resonance Imaging, vol. 36, No. 1, pp. 55-72, 13. Jun. 2012 //.

Mansfield, P "Real-Time Echo-Planar Imaging By NMR" British Medical Bulletin, vol. 40, No. 2, pp. 187-190, Jun. 1984 // https://doi.org/10.1093/oxfordjournals.bmb.a071970.

Heidemann, Robin et al. "A brief review of parallel magnetic resonance imaging" European Radiology, vol. 13, pp. 2323-2337, 2003.

Haase, A. et al. "FLASH Imaging. Rapid NMR Imaging Using Low Flip-Angle Pulses" Journal of Magnetic Resonance, vol. 67, pp. 258-266, 1986.

Griswold, Mark A. et al. Generalized Autocalibrating Partially Parallel.

Akeson, P. et al. "Time-dependency in brain lesion enhancement with gadodiamide injection" ACTA Radiologica, vol. 38, No. 1, pp. 19-24, 1997 // https://doi.org/10.1080/02841859709171236.

Woodfiled, Julie et al. "Magnetic resonance imaging acquisition techniques intended to decrease movement artefact in paediatric brain imaging: a systematic review" Pediatric Radiology, vol. Sep. 2015 //.

Extended European Search Report for corresponding Application No. 17872305.2, dated Jun. 8, 2020.

Graif et al. "Contrast-Enhanced MR Imaging of Malignant Brain Tumors" AJNR: 6, pp. 855-862 (1985).

Nael, Kambiz et al. "Six-minute magnetic resonance imaging protocol for evaluation of acute ischemic stroke: pushing the boundaries" Stroke, vol. 45, No. 7, pp. 1985-1991, Jul. 2014 // https://doi.org/10.1161/STROKEAHA.114.005305.

Gutierrez, Juan E. et al. Safety and Efficacy of Gadobutrol for Contrast-enhanced Magnetic Resonance Imaging of the Central Nervous System: Results from a Multicenter, Doubleblind, Randomized, Comparator Study Magnetic Resonance Insights, vol. 8, pp. 1-10, 2015.

Soman, S. et al. "Improved T2* Imaging without Increase in Scan Time: SWI Processing of 2D Gradient Echo", American Journal of Neuroradiology, vol. 34, No. 11, pp. 2092-2097, 2013.

Zhu, Yudong et al. "Highly Parallel Volumetric Imaging With a 32-Element RF Coil Array" Magnetic Resonance in Medicine, vol. 52, No. 4, pp. 869-877, Oct. 2004 // https://doi.org/10.1002/mrm.20209.

* cited by examiner

METHOD FOR RECORDING DIAGNOSTIC MEASUREMENT DATA OF A HEAD OF AN EXAMINATION OBJECT IN HEAD IMAGING VIA A MAGNETIC RESONANCE DEVICE

PRIORITY STATEMENT

The present application is a continuation of U.S. application Ser. No. 15/695,211, filed on Sep. 5, 2017, which is a continuation of and claims priority under 35 U.S.C. §§ 120 and 365(c) to PCT International Application No. PCT/US2017/048345 with an International Filing date of Aug. 24, 2017, which claims priority under 35 U.S.C. § 119 to U.S. Provisional Application No. 62/424,570 filed Nov. 21, 2016, the entire contents of each of which are hereby incorporated by reference.

FIELD

The invention relates to a method for recording diagnostic measurement data of a head of an examination object in head imaging via a magnetic resonance device, a magnetic resonance device and a computer program product.

BACKGROUND

In a magnetic resonance device, also referred to as a magnetic resonance imaging system, the body of an examination object to be examined, for example, of a patient, a healthy subject, an animal or a phantom, is usually exposed to a relatively high main magnetic field, for example, of 1.5 or 3 or 7 Tesla, with the aid of a main magnet. In addition, gradient circuits are output with the aid of a gradient coil unit. By way of a high-frequency antenna unit high-frequency pulses, for example, excitation pulses, are then emitted via the appropriate antenna equipment resulting in the nuclear spins of certain atoms resonantly excited by these high-frequency pulses being tilted around a defined flip angle opposite the magnetic field lines of the main magnetic fields. Upon relaxation of the nuclear spins, high-frequency signals, so-called magnetic resonance signals, are emitted, which are received via the appropriate high-frequency antennae and then further processed. The desired image data can be finally reconstructed from the raw data acquired in this way.

U.S. Pat. No. 6,529,762 B1 describes a method that simplifies the operation of a magnetic resonance device and makes interaction of the operator largely unnecessary during the execution of the measurement or scan. U.S. Pat. No. 7,990,141 B2 describes a method for operation of a magnetic resonance system in which the creation of measurement protocols is significantly simplified. U.S. Pat. No. 8,190,232 B2 describes a method for automating brain scanning.

SUMMARY

Magnetic resonance imaging can be used particularly advantageously to record diagnostic image data of a head of the examination object in head imaging. The object of the invention is to specify an improved method for head imaging via a magnetic resonance device. Head imaging may be referred to as brain imaging. Acquiring images of a head generally includes acquiring images of the brain. This object is achieved by the features of the independent claims. Advantageous embodiments are described in the subclaims.

The method according to at least one embodiment of the invention for recording diagnostic measurement data of a head of an examination object in head imaging via a magnetic resonance device comprises the following method steps:

performing an overview scan of the head of the examination object, wherein overview measurement data is acquired in the overview scan, performing various diagnostic scans of the head of the examination object based on the acquired overview measurement data, wherein diagnostic measurement data is acquired in the various diagnostic scans.

One embodiment provides that the head imaging comprises a maximum of one user interaction.

One embodiment provides that the number of diagnostic scans is at least three.

One embodiment provides that the measurement layers of at least two diagnostic scans correspond.

One embodiment provides that at least two diagnostic scans have a different orientation.

One embodiment provides that based on the overview measurement data for the diagnostic scans, necessary parameters and/or adjustments are determined individually for the examination object in one evaluation step.

One embodiment provides that recording parameters of the diagnostic scans and the overview scans are coordinated in such a way that head imaging is concluded within an imaging period not exceeding a maximum of 10 minutes.

One embodiment provides that the examination object only remains in the magnetic resonance device for the period of imaging.

One embodiment provides that each diagnostic scan has its own contrast which is one of the following: a T1 contrast, a T2 contrast, a FLAIR-contrast, a susceptibility contrast, a diffusion-weighted contrast.

One embodiment provides that head imaging comprises the administration of contrast agent and the number of diagnostic scans is at least eight.

One embodiment provides that chronologically before the administration of contrast agent, an overview scan and at least three diagnostic scans take place and chronologically after the administration of contrast agent at least two diagnostic scans take place.

One embodiment provides that at least one of the at least two diagnostic scans which take place chronologically after the administration of contrast agent is insensitive to the contrast agent administered, and at least one of the at least two diagnostic scans which take place chronologically after the administration of contrast agent is sensitive to the contrast agent administered.

One embodiment provides that within a waiting period between the administration of contrast agent and the start of at least two diagnostic scans which takes place chronologically after the administration of contrast agent and is sensitive to the contrast agent administered, one of the at least two diagnostic scans which takes place chronologically after the administration of contrast agent and is insensitive to the contrast agent takes place.

One embodiment provides that at least two diagnostic scans which take place chronologically after the administration of contrast agent, are insensitive to the contrast agent administered and the sequence of the at least two diagnostic scans is variable.

One embodiment provides that the sequence of the at least three diagnostic scans which take place chronologically before the administration of contrast agent is variable.

One embodiment provides that at least one diagnostic scan which takes place chronologically before the administration of contrast agent is only distinguished from at least one diagnostic scan which takes place chronologically after the administration of contrast agent by the timing of the diagnostic scans.

One embodiment provides that the diagnostic scan produces a T1 contrast.

One embodiment provides that each diagnostic scan has its own contrast which is one of the following: a T1 contrast, a T2 contrast, a FLAIR contrast, a susceptibility contrast, a diffusion-weighted contrast, a GM-WM-T1 contrast in which the contrast between Gray Mass and White Mass is greater compared to the T1 contrast.

One embodiment provides that recording parameters of the overview scan and the diagnostic scans, and their sequence, are coordinated in such a way that head imaging is concluded within an imaging period not exceeding a maximum of 19 minutes.

The magnetic resonance device according to at least one embodiment of the invention comprises a measurement data acquisition unit and a computing unit, wherein the magnetic resonance device is designed to perform a method according to at least one embodiment of the invention.

Thus, the computing unit in particular is designed to execute computer-readable instructions to perform the method according to at least one embodiment of the invention. In particular, the magnetic resonance device comprises a storage unit, wherein computer-readable information is stored on the storage unit, wherein the computing unit is designed to load the computer-readable information from the storage unit and to execute the computer-readable information to perform a method according to at least one embodiment of the invention.

The computing unit can be designed to transmit control signals to the magnetic resonance device, in particular to the measurement data acquisition unit of the magnetic resonance device and/or to receive and/or process control signals to perform a method according to at least one embodiment of the invention. The computing unit can be integrated in the magnetic resonance device. The computing unit can also be installed separately from the magnetic resonance device. The computing unit can be connected to the magnetic resonance device.

To provide support for the performance of the method according to at least one embodiment of the invention, the computing unit can be designed in several sub-computing units which support the performance of various tasks for head imaging or perform these various tasks.

Thus, a first sub-computing unit of the computing unit can be designed as a service computer, also referred to as a host computer. The service computer is, in particular, designed to prepare and process user interactions. Furthermore, the service computer can be designed to control the magnetic resonance device for the performance of head imagings. Furthermore, the service computer can already further process reconstructed image data in the overview scans and diagnostic scans. The further processing of image data by the host computer may, for example, comprise an evaluation of the image data, for example, a determination of a spatial extent of a particular tissue. Further processing of the image data by the host computer may alternatively or in addition, also comprise a calculation of recording parameters for the following measurements on the basis of the image data.

A second sub-computing unit of the computing unit can be designed as a reconstruction computer. The reconstruction computer is, in particular, designed to reconstruct image data from the overview measurement data and diagnostic measurement data. The reconstruction computer can exchange data with the service computer for this purpose. The reconstruction computer can, in particular, be integrated into the magnetic resonance device. The reconstruction computer can reconstruct already acquired measurement data parallel to the acquisition of additional measurement data. In such a manner, reconstructed image data can already be available for further processing by the service computer during the performance of head imaging in the sense of "inline-processing". The reconstruction computer can also take over part of the further processing of reconstructed image data, in particular for the calculation of recording parameters for the following measurements. In such a manner, the reconstruction computer can, for example, be designed to recognize landmarks on image data to automatically determine a recording area.

The components of the computing unit of the magnetic resonance device according to at least one embodiment of the invention can predominantly be designed in the form of software components. In principle, however, some these components can also be realized, especially where particularly rapid calculations are involved, in the form of software-supported hardware components, for example, FPGAs or the like. Likewise, the requisite interfaces can, for example, be designed as software interfaces if it is only a matter of the transfer of data from other software components. However, they can also be designed as hardware interfaces which are controlled by appropriate software. Naturally, it is also conceivable that several of the aforementioned components are combined in the form of an individual software component or software-supported hardware components.

BRIEF DESCRIPTION OF THE DRAWINGS

Hereinafter the invention is described and explained in more detail with reference to the exemplary embodiments shown in the figures.

The figures show.

DETAILED DESCRIPTION OF EXAMPLE EMBODIMENTS

Figure 1:
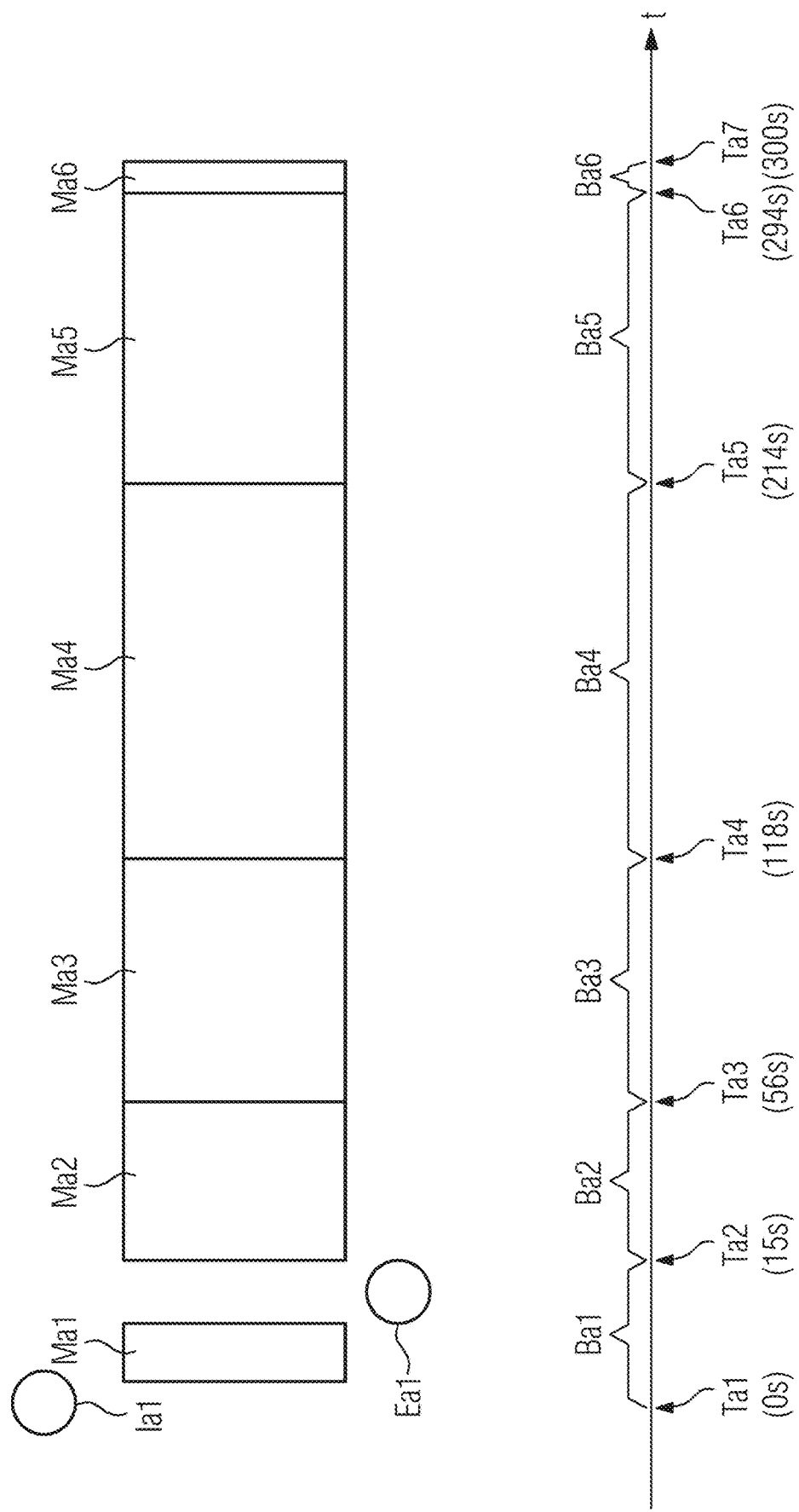
FIG. 1 illustrates a sequence of a first head imaging according to an example embodiment, FIG. 2 a sequence of a second head imaging according to an example embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, the term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules.

Group memory hardware encompasses a memory device that, in combination with other memory devices, stores some or all code from one or more modules.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention for recording diagnostic measurement data of a head of an examination object in head imaging via a magnetic resonance device comprises the following method steps:

performing an overview scan of the head of the examination object, wherein overview measurement data is acquired in the overview scan, performing various diagnostic scans of the head of the examination object based on the acquired overview measurement data, wherein diagnostic measurement data is acquired in the various diagnostic scans.

One embodiment provides that the head imaging comprises a maximum of one user interaction.

One embodiment provides that the number of diagnostic scans is at least three.

One embodiment provides that the measurement layers of at least two diagnostic scans correspond.

One embodiment provides that at least two diagnostic scans have a different orientation.

One embodiment provides that based on the overview measurement data for the diagnostic scans, necessary parameters and/or adjustments are determined individually for the examination object in one evaluation step.

One embodiment provides that recording parameters of the diagnostic scans and the overview scans are coordinated in such a way that head imaging is concluded within an imaging period not exceeding a maximum of 10 minutes.

One embodiment provides that the examination object only remains in the magnetic resonance device for the period of imaging.

One embodiment provides that each diagnostic scan has its own contrast which is one of the following: a T1 contrast, a T2 contrast, a FLAIR-contrast, a susceptibility contrast, a diffusion-weighted contrast.

One embodiment provides that head imaging comprises the administration of contrast agent and the number of diagnostic scans is at least eight.

One embodiment provides that chronologically before the administration of contrast agent, an overview scan and at least three diagnostic scans take place and chronologically after the administration of contrast agent at least two diagnostic scans take place.

One embodiment provides that at least one of the at least two diagnostic scans which take place chronologically after the administration of contrast agent is insensitive to the contrast agent administered, and at least one of the at least two diagnostic scans which take place chronologically after the administration of contrast agent is sensitive to the contrast agent administered.

One embodiment provides that within a waiting period between the administration of contrast agent and the start of at least two diagnostic scans which takes place chronologically after the administration of contrast agent and is sensitive to the contrast agent administered, one of the at least two diagnostic scans which takes place chronologically after the administration of contrast agent and is insensitive to the contrast agent takes place.

One embodiment provides that at least two diagnostic scans which take place chronologically after the administration of contrast agent, are insensitive to the contrast agent administered and the sequence of the at least two diagnostic scans is variable.

One embodiment provides that the sequence of the at least three diagnostic scans which take place chronologically before the administration of contrast agent is variable.

One embodiment provides that at least one diagnostic scan which takes place chronologically before the administration of contrast agent is only distinguished from at least one diagnostic scan which takes place chronologically after the administration of contrast agent by the timing of the diagnostic scans.

One embodiment provides that the diagnostic scan produces a T1 contrast.

One embodiment provides that each diagnostic scan has its own contrast which is one of the following: a T1 contrast, a T2 contrast, a FLAIR contrast, a susceptibility contrast, a diffusion-weighted contrast, a GM-WM-T1 contrast in which the contrast between Gray Mass and White Mass is greater compared to the T1 contrast.

One embodiment provides that recording parameters of the overview scan and the diagnostic scans, and their sequence, are coordinated in such a way that head imaging is concluded within an imaging period not exceeding a maximum of 19 minutes.

The proposed procedures for head imaging(s) may have the advantage that very high quality image data of the head of the examination object can be recorded. In such a manner, via the acquired image data a multiplicity of possible diseases and/or pathologies of the head of the examination object can be detected particularly advantageously where they occur. Naturally, additional indications appearing useful to a person skilled in the art can also be examined via the acquired image data. Thus, for example, lesions with diffusion restriction can be determined particularly advantageously. Alternatively, or in addition, further tissue and/or fluid properties and/or a function and/or an activity of the brain can also be ascertained. A diagnosis of a stenosis and/or a stroke may also be possible.

Precisely a possible integrated evaluation of the acquired measurement data (so-called inline processing) can lead to a reduction in the time until the final examination results and/or examination reports are available. The integrated evaluation of the acquired measurement data for the preparation of diagnostic information can take place in full after conclusion of the acquisition of all the measurement data. Alternatively, it is also conceivable that diagnostic measurement data is already being reconstructed and/or evaluated as long as the acquisition of additional measurement data of the examination object is still going on. The integrated evaluation of the acquired measurement data can be used for the integrated evaluation of measurement data of the examination object acquired during a measuring block to determine recording parameters, such as for example, the positioning of measurement layers and/or the size of a recording area or for the acquisition of measurement data of the examination object in a subsequent measuring block. Thus, the integrated evaluation of the acquired measurement data can fulfill a valuable dual role.

Furthermore, the proposed head imaging may have the advantage that the image data of the head of the examination object required for a particular diagnostic question can be recorded particularly quickly. At the same time, especially few movement artifacts may be present in the acquired image data. The proposed head imaging can therefore also be used advantageously for examination objects which do not behave cooperatively.

Furthermore, the proposed head imaging may have the advantage that it is particularly user-friendly and easy to use. It is advantageously conceivable that the proposed head imaging may also be performed by personnel who are not specially trained. Above all, the proposed automation can also enable an inexperienced user to acquire high-quality image data in the course of head imaging and/or the proposed minimization of necessary user interaction for head imaging. A standardized procedure for the proposed head imaging can also lead to consistent and easily comparable examination results.

The magnetic resonance device according to at least one embodiment of the invention comprises a measurement data acquisition unit and a computing unit, wherein the magnetic resonance device is designed to perform a method according to at least one embodiment of the invention.

Thus, the computing unit in particular is designed to execute computer-readable instructions to perform the method according to at least one embodiment of the invention. In particular, the magnetic resonance device comprises a storage unit, wherein computer-readable information is stored on the storage unit, wherein the computing unit is designed to load the computer-readable information from the storage unit and to execute the computer-readable information to perform a method according to at least one embodiment of the invention.

The computing unit can be designed to transmit control signals to the magnetic resonance device, in particular to the measurement data acquisition unit of the magnetic resonance device and/or to receive and/or process control signals to perform a method according to at least one embodiment of the invention. The computing unit can be integrated in the magnetic resonance device. The computing unit can also be installed separately from the magnetic resonance device. The computing unit can be connected to the magnetic resonance device.

To provide support for the performance of the method according to at least one embodiment of the invention, the computing unit can be designed in several sub-computing units which support the performance of various tasks for head imaging or perform these various tasks.

The computing unit may be hardware, firmware, hardware executing software or any combination thereof. When the computing unit is hardware, such existing hardware may include one or more Central Processing Units (CPUs), digital signal processors (DSPs), system on chips (SoCs), application-specific-integrated-circuits (ASICs), field programmable gate arrays (FPGAs) computers or the like configured as special purpose machines to perform the functions of the at least one of the image information generator 510, image information outputter 520, luminance compensation coefficient determiner 530, and color compensation coefficient determiner 540. CPUs, DSPs, ASICs and FPGAs may generally be referred to as processors and/or microprocessors.

In the event where the computing unit is a processor executing software, the processor is configured as a special purpose machine to execute the software to perform the functions of the computing unit. In such an embodiment, the processor may include one or more Central Processing Units (CPUs), digital signal processors (DSPs), application-specific-integrated-circuits (ASICs), field programmable gate arrays (FPGAs) computers.

Thus, a first sub-computing unit of the computing unit can be designed as a service computer, also referred to as a host computer. The service computer is, in particular, designed to prepare and process user interactions. Furthermore, the service computer can be designed to control the magnetic resonance device for the performance of head imagings. Furthermore, the service computer can already further process reconstructed image data in the overview scans and diagnostic scans. The further processing of image data by the host computer may, for example, comprise an evaluation of the image data, for example, a determination of a spatial extent of a particular tissue. Further processing of the image data by the host computer may alternatively or in addition, also comprise a calculation of recording parameters for the following measurements on the basis of the image data.

A second sub-computing unit of the computing unit can be designed as a reconstruction computer. The reconstruction computer is, in particular, designed to reconstruct image data from the overview measurement data and diagnostic measurement data. The reconstruction computer can exchange data with the service computer for this purpose. The reconstruction computer can, in particular, be integrated into the magnetic resonance device. The reconstruction computer can reconstruct already acquired measurement data parallel to the acquisition of additional measurement data. In such a manner, reconstructed image data can already be available for further processing by the service computer during the performance of head imaging in the sense of "inline-processing". The reconstruction computer can also take over part of the further processing of reconstructed image data, in particular for the calculation of recording parameters for the following measurements. In such a manner, the reconstruction computer can, for example, be designed to recognize landmarks on image data to automatically determine a recording area.

The components of the computing unit of the magnetic resonance device according to at least one embodiment of the invention can predominantly be designed in the form of software components. In principle, however, some these components can also be realized, especially where particularly rapid calculations are involved, in the form of software-supported hardware components, for example, FPGAs or the like. Likewise, the requisite interfaces can, for example, be designed as software interfaces if it is only a matter of the transfer of data from other software components. However, they can also be designed as hardware interfaces which are controlled by appropriate software. Naturally, it is also conceivable that several of the aforementioned components are combined in the form of an individual software component or software-supported hardware components.

Thus, the magnetic resonance device, in particular the measurement data acquisition unit and the computing unit, is designed to execute a method for recording diagnostic measurement data of a head of an examination object in head imaging using the following methods:

performing of an overview scan of the head of the examination object, overview measurement data being acquired in the overview scan, performing of several diagnostic scans of the head of the examination object based on the acquired overview measurement data, wherein diagnostic measurement data is acquired in the various diagnostic scans.

The computer program product according to at least one embodiment of the invention can be loaded directly into a storage unit of a programmable computing unit of a magnetic resonance device and has program code means to perform a method according to at least one embodiment of the invention if the computer program product is executed in the computing unit of the magnetic resonance device. The computer program product may be a computer program or include a computer program. As a result, the execution of the method according to at least one embodiment of the invention can be quick, identically reproducible and robust. The computer program product is configured such that it can perform the method steps according to at least one embodiment of the invention via the computing unit. The computing unit must satisfy each of the conditions such as, for example, a corresponding main memory, a corresponding graphic card or a corresponding logic unit so that the respective method steps can be efficiently performed. The computer program product is, for example, stored on a computer-readable medium or on a network or server from where it can be loaded into the processor of a local computing unit which is directly linked to the magnetic resonance device or can be designed as part of the magnetic resonance device. Furthermore, control information from the computer program product can be stored on a machine-readable data medium. The control information of the machine-readable data medium can be designed such that it performs a method according to at least one embodiment of the invention when the data medium is used in a computing unit of the magnetic resonance device. Thus, the computer program product can also represent the machine-readable data medium. Examples of machine-readable data media are a DVD, a magnetic tape, a hard disk or a USB stick on which machine-readable control information, in particular software (see above), is stored. If this control information (software) is read from the data medium and stored in a control and/or computing unit of the magnetic resonance device, all the embodiments according to at least one embodiment of the invention of the aforementioned method can be performed. Thus, the invention can also originate from the computer-readable medium in question and/or the electronically-readable data medium.

The advantages of the magnetic resonance device according to at least one embodiment of the invention and the computer program product according to at least one embodiment of the invention essentially correspond to the advantages of the method according to at least one embodiment of the invention previously described in detail. Features, advantages or alternative embodiments mentioned here are likewise also to be transferred to the other claimed objects and vice versa. In other words, the claims in question can also be developed with the features which are described or claimed in connection with a method. The corresponding functional features of the method are embodied by corresponding representational modules, in particular by hardware modules.

General Preliminary Remarks Regarding the Description of Head Imagings

Figure 2:
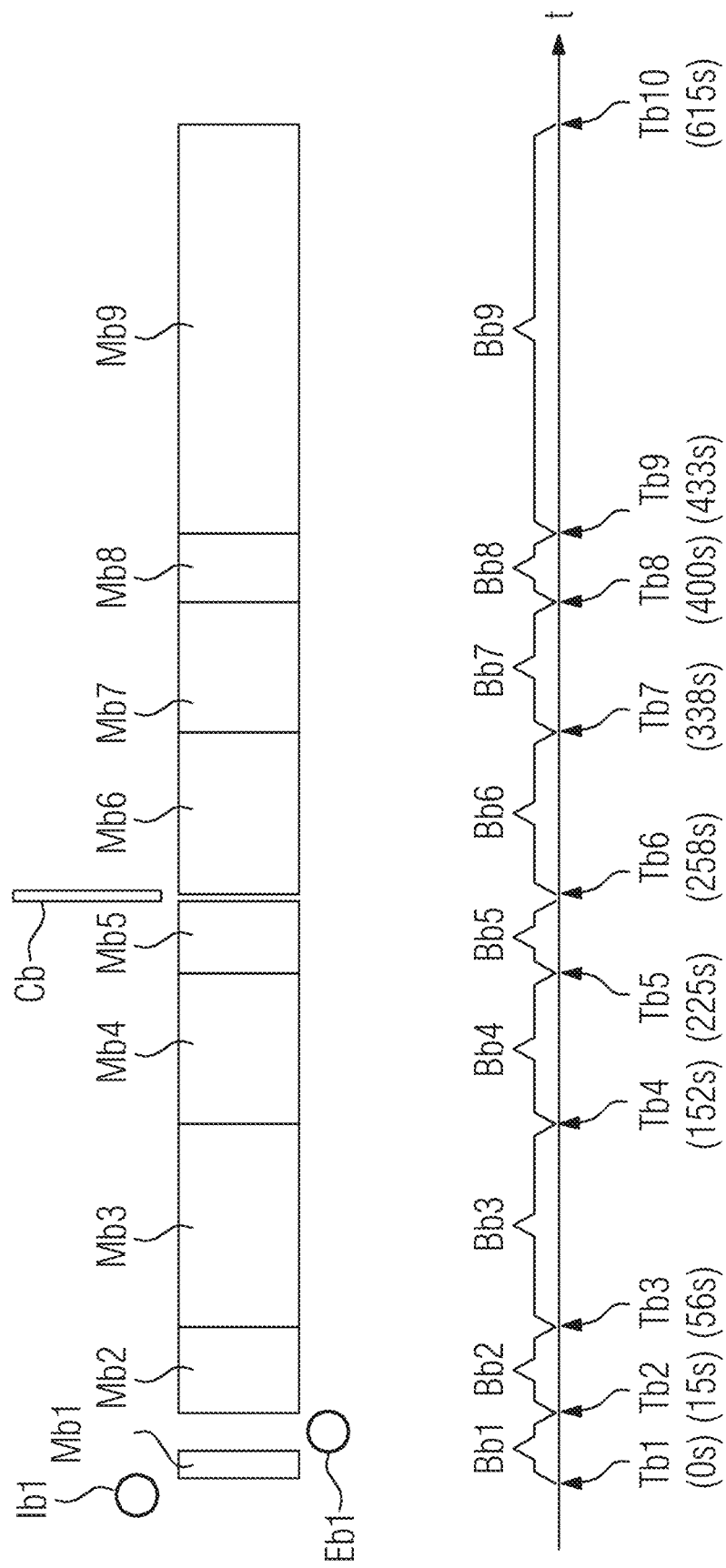

In FIGS. 1-2, two possible head imaging sequences are shown. Thus, in FIG. 1 a sequence of a first head imaging is shown. FIG. 2 shows a sequence of a second head imaging.

In the respective description of the figures, first the concrete sequence or workflow for the respective head imaging is described for each head imaging. Then various acceleration techniques and automation techniques are explained for the respective head imaging and underlying principles. The description of the head imagings in FIGS. 1-2 is based on the use of a magnetic resonance device with a main magnetic field with a strength of 3 Tesla and a receive unit with 32 reception channels. When using a different main magnetic field strength and/or a different receive unit, the head imagings of the head imagings shown in FIGS. 1-2, in particular the precise periods and/or recording parameters, may differ. This is described separately.

The head imagings presented in FIGS. 1-2 in particular represents a measuring session in each case in which the examination object is examined via the magnetic resonance device. In this manner, the examination object remains positioned in the magnetic resonance device throughout the entire sequence of a presented head imaging. In particular, the positioning of the patient bed and/or the positioning of the brain of the patient in the magnetic resonance device does not change or preferably only after completion of the overview scan and before the start of the diagnostic scans of respective head imaging.

In each case, the head imaging described is divided into several, in particular immediately, consecutive measuring blocks Ba, Bb. In each measuring block Ba, Bb in particular, in each case a recording Ma, Mb of measurement data takes place. Besides the recording Ma, Mb of the measurement data, a measuring block Ba, Bb may comprise a user interaction regarding the preparation of the recording Ma, Mb.

The recording may be an overview scan in which overview measurement data is acquired. The overview measurement data is mainly, possibly exclusively, provided for the determination of recording parameters of a recording Ma, Mb which takes place in one of the following measuring blocks Ba, Bb. The overview measurement data is primarily used to determine recording parameters for a measurement in a subsequent measuring block Ba, Bb. From the overview measurement data, furthermore, image data, in particular overview image data, can also be reconstructed and are stored in a database. The determination of recording parameters for a subsequent recording usually takes place with the aid of the overview image data; thus, for example, via the overview image data the layer positioning, the layer orientation and/or the layer spacing are determined.

However, the overview image data reconstructed from the overview measurement data is usually not of key interest for a diagnosis. The overview measurement data can also be stored together with the overview image data. As a rule, overview measurement data is only shown to a doctor for the diagnosis insofar as they show him the point at which the actual diagnostic image data was recorded. Thus, in the overview measurement data, for example, the position or positions which indicate the position of the actual diagnostic image data in the body can be marked. In some cases, it is also conceivable that the overview measurement data is not stored in a database and after being used to determine recording parameters are discarded again.

Alternatively, or in addition, the recording Ma, Mb can be a diagnostic scan in which diagnostic measurement data is acquired. From the diagnostic measurement data, in particular diagnostic image data can be generated which can be displayed for a diagnosing doctor on a display unit. In particular, therefore, the diagnostic measurement data present data which is reconstructed as image data which in a later diagnostic diagnosis are shown to a doctor to make the actual diagnosis by way of the image data. From the diagnostic measurement data, alternatively or in addition, physiological parameters of the head of the examination object can be calculated which can be made available to the diagnosing doctor. In a recording of diagnostic measurement data, no diagnosis in the proper sense is activated. Only diagnostic measurement data is recorded and if necessary, reconstructed as diagnostic image data which in its entirety enables a trained radiologist to recognize an adequate range of neurological diseases. If necessary, a diagnosis can be made on the basis of the diagnostic measurement data. In addition, the diagnostic measurement data can also be used to determine recording parameters of a recording Ma, Mb which takes place in one of the following measuring blocks Ba, Bb. In the first head imaging and in the second head imaging, the determination of recording parameters takes place from a recording Ma, Mb preferably based on the overview measurement data.

In addition, the measuring blocks Ba, Bb may also comprise an evaluation step Ea, Eb in which the measurement data acquired during the respective measuring block Ba, Bb is evaluated. The evaluation of the measurement data takes place in the evaluation step Ea, Eb in particular, immediately after the acquisition of the measurement data. The evaluation of the measurement data in the evaluation step Ea, Eb typically provides information to determine recording parameters from a recording Ma, Mb which takes place in one of the following measuring blocks Ba, Bb. Before determining the recording parameters, typically a reconstruction of image data is already performed from the overview measurement data, wherein the recording parameters can then be determined on the basis of image data. Alternatively, the measurement data in the evaluation step Ea, Eb can also only be reconstructed to such an extent that only the determination of the recording parameters from a recording which takes place in one of the following measuring blocks is possible on the basis of the reconstructed image data.

The automatic determination of the recording parameters can take place, in particular algorithmic, evaluation of overview image data which has been reconstructed from the acquired overview measurement data. If an evaluation of overview measurement data to determine recording parameters for a measurement in a subsequent measuring block Ba, Bb takes place in the evaluation step Ea, Eb, the determination of the recording parameters and consequently the preparation of the diagnostic scans Ma2-Ma6 can take place particularly quickly. Overview image data reconstructed from the overview measurement data can be reconstructed in a fraction of the time of the associated measuring block and shown to a user on a user interface, for example, to validate the determination of the recording parameters. Recording parameters can thus be automatically proposed to a user and a user can decide to either accept or modify the proposal.

In addition, the measuring blocks Ba, Bb may also comprise user interaction Ia, Ib. With user interaction Ia, Ib, in particular, preparation of head imaging takes place, wherein the examination object, in particular of the patient, is positioned. User interaction Ia, Ib may comprise the input of a user command by way of an appropriate input unit. In the user interaction Ia, Ib, recording parameters for the recording Ma, Mb can be entered in the respective measuring block Ba, Bb and/or for a subsequent recording Ma, Mb. In the user action Ia, Ib, naturally recording parameters can also be changed.

The depiction of the head imagings in the FIGS. 1-2 is always along a horizontal timeline t which is arranged at the bottom of the figures. On the timeline, in each case several points in time Ta, Tb are plotted several times. The points in time are starting and ending times of measuring blocks Ba, Bb; the temporal period and arrangement of which is plotted immediately above the horizontal timeline. For each measuring block Ba, Bb, the respective recording Ma, Mb is plotted as a box. Indications for the temporal period of the recordings Ma, Mb and the positioning of the recordings Ma, Mb within the respective measuring block Ba, Bb can be read out from the FIGS. 1-2. Of course, temporal periods of the recordings Ma, Mb different from the depiction and different positioning of the recordings Ma, Mb inside the respective measuring block Ba, Bb are also conceivable, however.

Possible user interactions Ia, Ib taking place in the measuring block Ba, Bb are plotted as a circle over the recordings Ma, Mb. Possible evaluation steps Ea, Eb taking place in the measuring block Ba, Bb are plotted as a circle under the recordings Ma, Mb. The user interactions Ia, Ib and evaluation steps Ea, Eb are plotted with an exemplary period at their respective typical temporal position inside the head imaging. Reference points for the temporal positioning of the user interactions Ia, Ib and evaluation steps Ea, Eb inside the respective measuring block Ba, Bb can be read from the FIGS. 1-2. Naturally, however, different temporal positioning and temporal periods of the user interactions Ia, Ib and evaluation steps Ea, Eb inside the respective measuring block Ba, Bb are also conceivable from the depiction.

FIG. 1—First Head Imaging

General Information about the First Head Imaging

The first head imaging, the sequence of which is shown in FIG. 1, in particular provides diagnostic measurement data which can serve as the basis for an assessment of the anatomy and/or pathology of the head of the examination object. Preferably, the first head imaging can take place so thoroughly that a multiplicity of possible diseases and/or pathologies of the head of the examination object can be detected when they occur. Examples of such diseases are intracranial mass-like lesions, intracranial hemorrhage, ischemia and other lesions with diffusion restriction, white matter hyperintensities, subarachnoid FLAIR hyperintensities, and hydrocephalus. In principle, gray-white matter differentiation should also take place. In particular, it is an objective of the first head imaging to record the diagnostic measurement data required for the assessment of the anatomy and/or pathology of the head of the examination object in a short first imaging period, compared with traditional, comparable examinations of the head via a magnetic resonance device. The diagnostic measurement data is preferably recorded in the short first imaging period such that the anatomy and/or pathology of the head can be ascertained and provided in sufficient quality despite the comparatively short first imaging period.

The first head imaging has a first imaging period which elapses from a starting time Ta1 of the first head imaging until a seventh point in time Ta1, in which the recording of measurement data in the first head imaging is finished. The first imaging period is preferably 10 minutes maximum, advantageously 8 minutes maximum and particularly advantageously 6 minutes maximum, most advantageously 5 minutes maximum.

The first imaging period is, in particular, dependent on the choice of the receive unit which is used to receive magnetic resonance signals. The higher the number of individual receive channels of the receive unit employed, the shorter the first imaging period can be. A variability of the first imaging period is given, in particular analogous to the specified areas, or to the variability for the period of the measuring blocks comprised by the first imaging. The first imaging period is, in particular, designed as a maximum imaging period which ideally is not exceeded for the performance of the first head imaging. A period of user interactions or parameter settings can be included in the first imaging period for the acquisition of measurement data. In certain cases, it is also conceivable that a period of patient positioning is included in the first imaging period. Alternatively, the first imaging period may also be characterized by the fact that more than 60 percent, in particular more than 75 percent, most advantageously more than 90 percent of a series of various examinations which are performed in accordance with the diagram in FIG. 1 for the first head imaging in the clinical routine include the first imaging period.

FIG. 1 shows the particularly advantageous case in which the first imaging period of the first head imaging lasts 5 minutes. After completion of the recording of the measurement data in the first head imaging, further time may elapse in which subsequent processing and/or evaluation of the measurement data takes place. However, the examination object must only remain in the magnetic resonance device during the first imaging period. After the first imaging period, a subsequent examination object can be positioned in the magnetic resonance device as a result of which better utilization of the device can be achieved.

Description of a Possible Concrete Sequence of the First Head Imaging

Preparation of the First Head Imaging

Firstly, in particular, it is established that head imaging of the examination object should be performed. A maximum imaging period of the first head imaging can be determined, wherein the maximum imaging period in particular may not be exceeded by first imaging period. The establishment of the maximum imaging period can take place directly, for example, by a user entering the maximum imaging period for the entire examination sequence of the first head imaging directly into an input screen. The establishment of the maximum imaging period can also take place indirectly, for example, by the user selecting a variant linked to the maximum imaging period, in particular the first head imaging from a multiplicity of different established procedures for head imaging, for example, by way of an interaction on a user interface. Once a maximum imaging period is established, a user obtains planning security for the period and/or feasibility of the first head imaging.

Before the starting time Ta1 of the first head imaging, patient-specific features can be automatically or manually recorded. Imaging parameters for the first head imaging can then be adjusted by way of the patient-specific features. The subsequent temporal sequence of the individual measuring blocks can be varied on the basis of the specific input of the patient-specific feature and as a function thereof.

A possible patient-specific feature is a language which is to be used for commands to the examination object. Furthermore, for example, the height of the examination object can be recorded. A typical position of the head of the examination object can be estimated using the height, enabling the head of the examination object to be positioned in approximately the isocenter of the magnetic resonance device or in the field of view of the magnetic resonance device before the recording of the first measurement data.

After entering the patient-specific features and appropriately positioning the patient support device on which the examination object is supported in the magnetic resonance device, the first head imaging can be started. The first head imaging starts, in particular, after activation of a start button by a user.

Measuring Block Ba1

The first head imaging displayed starts at a first point in time Ta1 or starting time Ta1 with a first measuring block Ba1. In the first measuring block Ba1, a first user interaction Ia1 takes place, an overview scan Ma1 during which first overview measurement data is acquired, and a first evaluation step Ea1.

In the case shown, the first measuring block Ba1 has a first period of 15 seconds. The first period is preferably between 5 seconds and 25 seconds, in particular between 10 and 20 seconds, in particular between 12 seconds and 17 seconds. Between 2 and 20 seconds, in particular between 9 and 18 seconds, in particular 14 seconds of the first period are in the pure measurement period of the first overview scan Ma1 for the acquisition of the first overview measurement data. In particular, only that time which is required for the acquisition of the magnetic resonance signals which constitute the measurement data, in other words, for the playing out of the actual magnetic resonance sequence for this section of the first measuring block Ba1, is designated as a pure measurement period. The pure measurement period may therefore only comprise a period for filling the k-space with the measurement data.

Another period of the first measuring block Ba1 is partly attributable to the first user interaction Ia1 and to the first evaluation step Ea1. The first user interaction Ia1 may, for example, comprise the preparation of the acquisition of the first overview measurement data. In particular, the first user interaction Ia1 may comprise the output of voice commands to the examination object. The first user interaction Ia1 may, for example, comprise the activation of a start button by a user at the beginning of the overview scan Ma1. If the first user interaction Ia1 comprises the preparation of the acquisition of the first overview measurement data, the first head imaging can also start automatically after completion of the preparations. Furthermore, adjustment measurements which, for example, comprise the adjustment of a transmitter and receiver voltage of the magnetic resonance device, can be made inside the first measuring block Ba1 before starting the first overview scan Ma1 in preparation for the acquisition of the measurement data.

The first overview scan Ma1 is performed from a head region of the examination object. The first overview scan Ma1 is therefore, in particular, a measurement which is used to establish the recording parameters for subsequent measuring blocks. After performance of the recording scheme shown in FIG. 1, it does not usually play a significant role in the further diagnosis of the diagnostic measurement data. Thus, the first overview scan Ma1 can also generally speaking be described as a localizer measurement or scout measurement. The overview measurement data recorded in the first overview scan Ma1 comprises, in particular, several low-resolution measurement layers, advantageously in various layer orientations. In particular, the layer orientations in which the first overview scan Ma1 was produced differ from the layer orientations in which the subsequent measurement data is recorded in that the layer orientations for the first overview scan Ma1 are tilted in relation to the subsequent layer orientations.

The first overview scan Ma1 can be performed in accordance with DE102011079503 A1 and in particular take place in two stages. Thus, the first overview measurement data may comprise two datasets, which two datasets at least partly comprise an equal section of the area under examination. When reconstructing as image data, a first dataset of the two datasets preferably has a lower resolution than a second dataset of the two datasets. The first overview scan Ma1 is preferably designed in such a way that based on the first overview measurement data, the parameters and/or adjustments necessary for the subsequent recordings can be determined individually for the examination object in the first evaluation step Ea1. This preferably takes place automatically and is therefore robust, replicable and independent of the user, in particular, objective. The first overview scan Ma1 is typically performed with a gradient echo magnetic resonance sequence.

The first overview scan Ma1 is designed as a three-dimensional image of the head. To acquire the first overview measurement data Ma1, a gradient echo magnetic resonance sequence is preferably used which, for example, is implemented as a Fast Low-Angle Shot (FLASH) magnetic resonance sequence.

The recording area which is recorded by the first overview scan Ma1 is a volume which is phase-coded in a first direction and in a second direction and frequency-coded in a third direction. The second direction is perpendicular to the first direction and the third direction is perpendicular to the first and to the second direction. The first direction and the second direction preferably define a sagittal layer orientation. The pixel resolution is preferably isotropic. As a result, the orientation and/or tilting of the measurement layers for at least one diagnostic scan can typically be determined with particular precision. As a pixel resolution in the first direction and/or in the second direction and/or in the third direction, a range of between 1.0 mm and 2.2 mm, preferably a range of between 1.3 mm and 1.9 mm and particularly preferably a range of between 1.5 mm and 1.7 mm has proved appropriate. In particular, in the third direction the aforementioned pixel resolution can be produced via interpolation, wherein the pixel resolution in the third direction which would result from the measured points in the k-space, for example, is lower by at least 10%, advantageously by at least 20% and most advantageously by 31%. By zero filling of the k-space, interpolated voxels can be produced which are of the same size in the first direction and in the second direction and in the third direction. In this way, the first period can be reduced without any visible decline in quality.

The recording area of the first overview scan Ma1 is preferably a volume which has a spatial expansion in the range of between 200 mm and 400 mm, preferably between 220 mm and 300 mm and particularly preferably of 260 mm in the first direction and/or in the second direction. The spatial expansion in the first direction and in the second direction preferably match. The spatial expansion of the recording area in the third direction is in the range of between 200 mm and 400 mm, preferably between 220 mm and 300 mm and particularly preferably between 240 mm and 250 mm. The second direction preferably connects an anterior and a posterior position of the head of the examination object. The first direction is preferably a lateral direction.

The high frequency pulse which is used to excite nuclear spins in the context of the gradient magnetic resonance sequence is, for example, between 2° and 20°, preferably between 5° and 15° and particularly preferably 8°. The number of voxels per measurement layer in the first direction is, for example, between 96 and 256, preferably between 125 and 195 and particularly preferably 160. The number of voxels in the second direction preferably corresponds to the number of voxels in the first direction.

The repetition time of the first overview scan Ma1 is preferably selected such that the repetition time preferably does not exceed the minimum repetition time by 20% maximum, preferably by 10% maximum, in particular. A period of less than 10 ms, preferably of less than 6 ms and particularly preferably of less than 4 ms is preferably selected as a repetition time. Preferably, the first overview scan Ma1 takes place with an echo time which preferably does not exceed the minimum echo time by 20% maximum, preferably by 10% maximum, in particular. The minimum echo time typically corresponds to the period between the high frequency pulse of excitation and the temporal focus of the echo, which period is at least required on account of the magnetic resonance device used and/the high-frequency pulses used for excitation and/or for refocusing. A period of less than 5 ms, preferably of less than 3 ms and particularly preferably of less than 2 ms is preferably selected as the echo time. The bandwidth of the frequency coding in the first overview scan Ma1 is typically in the range of between 450 Hertz per pixel and 650 Hertz per pixel, preferably between 400 Hertz per pixel and 500 Hertz per pixel.

To acquire the first overview measurement data, acceleration technology is preferably used. In particular, the use of parallel imaging is conceivable, which is preferably used with an acceleration factor of between 2 and 4, in particular preferably with an acceleration factor of 3. In particular, the use of Compressed Sensing acceleration technology is conceivable.

The aforementioned parameters concerning the magnetic resonance sequence for the first overview scan Ma1 are advantageously selected such that the first overview measurement data can be recorded in full in less than 30 seconds, in particular in less than 20 seconds, advantageously in less than 15 seconds with the magnetic resonance sequence used. Reconstructed image data can be reconstructed and provided from the first overview measurement data immediately after completion of the first overview scan Ma1.

Furthermore, the first evaluation step Ea1 can partly account for the remaining period of the first measuring block Ba1. The first evaluation step Ea1 may comprise an evaluation or subsequent processing of the first overview measurement data acquired during the first overview scan Ma1. Typically, the first overview measurement data is partly reconstructed to form overview image data. On the basis of the first overview measurement data acquired in the first overview scan Ma1, a position and/or orientation of the head of the examination object can be identified, in particular on the basis of landmarks. The identification of the position and/or orientation of the head preferably takes place automatically in the first evaluation step Ea1. Alternatively, the identification of the position and/or orientation of the head can take place manually or semi-automatically. On the basis of the position of the head identified, the patient positioning device of the magnetic resonance device is preferably repositioned such that the head of the examination object is positioned in the isocenter of the magnetic resonance device. Thus, the following recordings Ma2, Ma3, Ma4, Ma5, Ma6 can be performed in the following measuring blocks Ba2, Ba3, Ba4, Ba5, Ba6 of the head of the examination object positioned in the isocenter.

Overall, the head is not yet specifically positioned in the isocenter (or only by chance or in the vicinity of the isocenter) for the recording of the first overview measurement data in the first measuring block Ba1, while on the basis of the first overview measurement data a repositioning of the patient can take place for the following measuring blocks Ba2, Ba3, Ba4, Ba5, Ba6 so that when recording the additional measurement data of the subsequent measuring blocks Ba2, Ba3, Ba4, Ba5, Ba6, the head is more precisely in or closer to the isocenter than during the first measuring block Ba1.

In the first evaluation step Ea1, positioning data can be extracted from the first overview measurement data. The positioning data comprises, in particular, the spatial position of the examination object relative to the magnetic resonance device and/or a plane of symmetry in the head of the examination object and/or the identified position and/or orientation of the head and/or information for the repositioning of the patient positioning device. Based on the positioning data, in the context of the first evaluation steps Ea1 and/or in the context of a subsequent measuring block Ba2, Ba3, Ba4, Ba5, Ba6, measurement layers or their positioning and/or their orientation and/or a recording area and/or if applicable, phase oversampling can be determined for at least one of the following recordings Ma2, Ma3, Ma4, Ma5, Ma6. The positioning data can be provided for the subsequent measuring blocks Ba2, Ba3, Ba4, Ba5, Ba6.

In the context of the first evaluation steps Ea1 and/or in the context of a subsequent measuring block Ba2, Ba3, Ba4, Ba5, Ba6, based on the positioning data of the recording area at least one of the subsequent recordings Ma2, Ma3, Ma4, Ma5, Ma6 can preferably be defined such that the center of the head of the examination object is positioned in the center of the recording area and/or an axis of symmetry of the head of the examination object matches an axis of symmetry of the recording area. The measurement layers can also be positioned such that the recording area is covered uniformly. The following recordings Ma2, Ma3, Ma4, Ma5, Ma6 can each cover different recording areas. The following measuring blocks Ba2, Ba3, Ba4, Ba5, Ba6 can typically be performed chronologically after completion of the first measuring block Ba1 in chronologically arbitrary sequence.

The first measuring block Ba1, in particular the first overview scan Ma1, is preferably independent of the receive unit and can be used with a magnetic resonance device which has a main magnetic field of 3 Tesla. If the first overview scan Ma1 is performed with a magnetic resonance device which has a main magnetic field of 1.5 Tesla, in particular the repetition time and the echo time may vary. The repetition time at 1.5 Tesla is preferably 4.5 ms and the echo time is preferably 2.4 ms.

Measuring Block Ba2

Following the first measuring block Ba1, at a second point in time Ta2, a second measuring block Ba2 starts during the first head imaging. In the second measuring block Ba2, a first diagnostic scan Ma2 takes place during which first diagnostic measurement data is acquired.

The second point in time Ta2 in the case shown is 15 s after the starting time Ta1 of the first head imaging. The second measuring block Ba2 in the case shown has a second period of 41 s. The second period is preferably between 20 seconds and 60 seconds, in particular between 30 and 50 seconds, in particular between 35 seconds and 45 seconds. The second period is preferably almost completely in the pure measurement period of the first diagnostic scan Ma2.

Furthermore, within the second measuring block Ba2 before the start of the first diagnostic scan Ma2 in preparation for the acquisition of measurement data, adjustment measurements can be performed which, for example, comprise the adjustment of a transmitter and receiver voltage of the magnetic resonance device. Such adjustment measurements are, in particular, performed for recordings, which recordings concern a recording area and/or a layer orientation, which recording area and/or which layer orientation differs from the previous recording. Such an adjustment measurement is typically attributed to a recording and a measuring block Ma, Mb comprises the recording and the adjustment measurement attributed to the recording.

In addition to the first diagnostic scan Ma2, the second measuring block Ba2 may comprise an adjustment measurement which typically lasts 15 seconds maximum, in particular 8 seconds maximum, in particular 5 seconds maximum, in particular 2 seconds maximum. The second period is typically extended by the duration of the adjustment measurement if an adjustment measurement is needed. A remaining period of the second measuring block Ba2 may be partly included in the preparation of the acquisition of the first diagnostic measurement data. For example, the recording area and/or the location of the measurement layers and/or the layer orientation for the first diagnostic scan Ma2 can be determined on the basis of the positioning data determined in evaluation step Ea1. The remaining period of the second measuring block Ba2 can furthermore be partly included in an evaluation or subsequent processing of the first diagnostic measurement data.

The first diagnostic scan Ma2 is a T1-weighted image of the head. To acquire the first diagnostic measurement data Ma2, a gradient echo magnetic resonance sequence is preferably used which, for example, is implemented as a Fast Low-Angle Shot (FLASH) magnetic resonance sequence. The acquisition of the recording area for the first diagnostic scan Ma2 preferably takes place two-dimensionally, wherein several measurement layers parallel to each other are recorded. A range of between 0.6 mm and 1.2 mm and particularly preferably 0.9 mm, has proved appropriate as pixel resolution within a measurement layer (in-plane resolution). Selection of the layer thickness, in other words the thickness of a measurement layer, of the first diagnostic scan Ma2 is preferably between 2 mm and 6 mm, preferably between 3 mm and 5 mm and particularly preferably 4 mm. The measurement layers exhibit a first layer orientation. The first layer orientation is preferably a sagittal layer orientation.

The distance between two adjacent measurements is preferably between 0% and 50% of the layer thickness, preferably between 10% and 30% of the layer thickness and particularly preferably 20% of the layer thickness. Typically, between 20 and 50 measurement layers, preferably between 30 and 40 measurement layers and particularly preferably 35 measurement layers are acquired. The recording area of the first diagnostic scan Ma2 is preferably a volume which has a spatial expansion in the range of between 100 mm and 250 mm, preferably between 150 mm and 200 mm and particularly preferably between 160 mm and 180 mm perpendicular to a measurement layer. The recording area of the first diagnostic scan Ma2 is preferably a volume which has a spatial expansion in the range of between 150 mm and 300 mm, preferably between 200 mm and 240 mm and particularly preferably of 220 mm within a measurement layer in a first direction. The recording area of the first diagnostic scan Ma2 preferably has a spatial expansion in the range of between 150 mm and 300 mm, preferably between 200 mm and 240 mm and particularly preferably of 220 mm in a second direction perpendicular to the first direction. The spatial expansion in the second direction preferably corresponds to the spatial expansion in the first direction.

For spatial encoding of the first direction a frequency coding is preferably used and for spatial encoding of the second direction a phase coding. The second direction preferably connects an anterior and a posterior position of the head of the examination object.

In the second direction measurement data acquisition, also referred to as phase oversampling, preferably takes place of an additional range beyond the spatial expansion of the area under examination. The additional range is preferably between 10% and 80%, in particular preferably between 30% and 50%, preferably 40% of the spatial expansion of the area under examination in the second direction. This can reduce and/or eliminate fold artifacts and/or increase the signal-to-noise ratio of the resulting image data. The bandwidth of the frequency coding for the first diagnostic scan Ma2 is typically in the range of between 200 Hertz per pixel and 500 Hertz per pixel and preferably between 300 Hertz per pixel and 400 Hertz per pixel. The bandwidth of the frequency coding for the first diagnostic scan Ma2 is preferably 360 Hertz per pixel.

The number of voxels per measurement layer in the first direction is preferably between 128 and 512 and particularly preferably between 200 and 300 and preferably 256. The number of voxels per measurement layer in the second direction preferably corresponds as a maximum to the number of voxels in the first direction, preferably the number of voxels in the direction perpendicular to the first direction is between 50% and 98%, preferably between 70% and 85% and particularly preferably 81% of the number of voxels in the first direction. The interpolation of voxels or zero-filling of the k-space can take place so that the interpolated voxels in the first direction and in the second direction are the same size.

A high frequency pulse which is used to excite nuclear spins in the context of the first diagnostic scan Ma2 preferably produces a defined flip angle between 60° and 90° and particularly preferably between 70° and 85° and preferably of 80°. A period in the range of between 200 ms and 280 ms, preferably between 220 ms to 260 ms and particularly preferably 240 ms is preferably selected as the repetition time. A period in the range of between 2 ms and 3 ms, preferably between 2.2 ms to 2.7 ms and particularly preferably 2.5 ms is preferably selected as the echo time.

Acceleration technology is preferably employed to acquire the first diagnostic measurement data. In particular, the use of parallel imaging is conceivable and is preferably used with an acceleration factor of 3 maximum, in particular preferably with an acceleration factor of 2. In particular, the use of Compressed Sensing acceleration technology is conceivable alternatively or in addition.

The aforementioned parameters regarding the magnetic resonance sequence for the first diagnostic scan Ma2 are advantageously selected such that the first diagnostic measurement data can be recorded in full with the magnetic resonance sequence used in less than 80 seconds, in particular in less than 60 seconds, advantageously in less than 50 seconds and most advantageously in less than 42 seconds. First image data reconstructed from the first diagnostic measurement data can be reconstructed and provided for diagnosis immediately after completion of the first diagnostic scan Ma2.

The second measuring block Ba2, in particular the first diagnostic scan Ma2, is dependent on the receive unit and the strength of the main magnetic field of the magnetic resonance device. The specified ranges of areas for parameters which are specified in the description of the second measuring block Ba2 for 3 Tesla and a receive unit with 32 reception channels are typically also valid for other configurations. The aforementioned embodiment of the first diagnostic scan Ma2 is preferably used at 3 Tesla and for receive units with up to 32, for example, with 16, 20 or 32 reception channels. If a receive unit with 64 reception channels is used at 3 Tesla, an acceleration factor of 4 maximum, preferably 3, and phase oversampling of 60% can be used whereby the second period can be reduced to less than 35 s.

If the first diagnostic scan Ma2 is performed with a magnetic resonance device with a main magnetic field with a strength of 1.5 Tesla, a spin echo magnetic resonance sequence is preferably used instead of the gradient echo magnetic resonance sequence. In addition to the underlying magnetic resonance sequence, the following parameters preferably change:

the layer thickness is 5 mm instead of 4 mm
the number of layers is reduced from 35 to 27
the repetition time is preferably between 200 ms and 280 ms and particularly preferably between 230 ms and 250 ms
the echo time is preferably less than 6 ms and particularly preferably less than 3 ms
a high frequency pulse to excite nuclear spins preferably produces a defined flip angle of 90°
the recording area in the first direction is preferably between 200 mm and 260 mm and particularly preferably between 220 mm and 240 mm
the bandwidth selected for frequency coding is preferably in the range of between 100 Hertz per pixel and 200 Hertz per pixel, preferably 150 Hertz per pixel
the resulting second period is typically between 60 s and 90 s, preferably between 70 s and 80 s.

Measuring Block Ba3

Following the second measuring block Ba2, a third measuring block Ba3 starts at a third point in time Ta3 during the first head imaging. A second diagnostic scan Ma3 takes place in the third measuring block Ba3, during which second diagnostic measurement data is acquired.

The third point in time Ta3 in the case shown is 56 s after the starting time Ta1 of the first head imaging. The third measuring block Ba3 in the case shown has a third period of 62 s. The third period is preferably between 40 seconds and 85 seconds, in particular between 50 and 75 seconds, in particular between 60 seconds and 70 seconds. Preferably, the third period is almost completely included in the pure measurement period of the second diagnostic scan Ma3. During the third measuring block Ba3, the first diagnostic measurement data can be at least partly reconstructed as image data and/or evaluated and/or processed, if necessary simultaneously with the recording of the second diagnostic scan Ma3.

Furthermore, in the third measuring block Ba3 before the start of the second diagnostic scan Ma3 in preparation for the acquisition of the measurement data an adjustment measurement which, for example, comprises an adjustment of a transmitter and/or receiver voltage of the magnetic resonance device, can be performed. The adjustment measurement typically lasts 15 seconds maximum, in particular 8 seconds maximum, in particular 5 seconds maximum, in particular 2 seconds maximum. If an adjustment measurement is required, the third period is typically extended by the duration of the adjustment measurement.

A remaining period of the third measuring block Ba3 can be partly included in the preparation of the acquisition of the second diagnostic measurement data. For example, based on the positioning data determined in evaluation step Eat, the recording area and/or the position of the measurement layers and/or the layer orientation for the second diagnostic scan Ma3 can be determined. The remaining period of the third measuring block Ba3 can furthermore be partly included in an evaluation or subsequent processing of the second diagnostic measurement data.

The second diagnostic scan Ma3 is a T2-weighted image of the head. To acquire the second diagnostic measurement data Ma3, a spin echo magnetic resonance sequence is preferably used which, for example, is implemented as a Turbo-spin-Echo (TSE) magnetic resonance sequence. The acquisition of the recording area for the second diagnostic scan Ma3 preferably takes place two-dimensionally, wherein various measurement layers in parallel to each other are recorded. A range of between 0.6 mm and 1.2 mm, and particularly preferably 0.9 mm, has proved suitable as the pixel resolution in a measurement layer (in-plane resolution). The layer thickness of the second diagnostic scan Ma3 selected is preferably between 3 mm and 7 mm, preferably between 4 mm and 6 mm and particularly preferably 5 mm. The measurement layers have a second layer orientation. The second layer orientation is preferably perpendicular to the first layer orientation and a transverse orientation.

The distance between two adjacent measurement layers is preferably between 0% and 50% of the layer thickness, preferably between 10% and 30% of the layer thickness and particularly preferably 20% of the layer thickness. Typically, between 10 and 40 measurement layers, preferably between 20 and 30 measurement layers and particularly preferably 25 measurement layers are acquired. The recording area of the second diagnostic scan Ma3 is preferably a volume which has a spatial expansion in the range of between 100 mm and 200 mm, preferably between 120 mm and 180 mm and particularly preferably between 140 mm and 160 mm perpendicular to a measurement layer. The recording area of the second diagnostic scan Ma3 is preferably a volume which has a spatial expansion in the range of between 150 mm and 300 mm, preferably between 200 mm and 240 mm and particularly preferably of 220 mm in a measurement layer in a first direction. The recording area of the second diagnostic scan Ma3 preferably has a spatial expansion in the range of between 150 mm and 230 mm, preferably between 170 mm and 210 mm and particularly preferably between 185 mm and 195 mm in a second direction perpendicular to the first direction. The spatial expansion in the second direction is preferably less than the spatial expansion in the first direction. Frequency coding is preferably used for spatial encoding of the first direction and phase coding is preferably used for spatial encoding of the second direction. The second direction is preferably a lateral direction.

The number of voxels per measurement layer in the first direction is preferably between 128 and 512 and particularly preferably between 200 and 300, preferably 256. The number of voxels per measurement layer in the second direction is preferably selected such that a second ratio between the spatial expansion in the second direction and the number of voxels in the second direction corresponds to a first ratio of the spatial expansion in the first direction and the number of voxels in the first direction maximum. The second ratio is preferably between 80% and 100%, preferably between 95% and 100% of the first ratio. The bandwidth of the frequency coding for the second diagnostic scan Ma3 is typically in the range of between 200 Hertz per pixel and 320 Hertz per pixel, preferably between 230 Hertz per pixel and 290 Hertz per pixel.

A high frequency pulse which is used for refocusing nuclear spins in the context of the second diagnostic scan Ma3 preferably produces a defined flip angle between 100° and 180° and particularly preferably between 110° and 130°, preferably of 120°. A period in the range of between 5000 ms and 10000 ms, preferably between 5500 ms and 7000 ms and particularly preferably of 6200 ms is preferably selected as the repetition time. A period in the range of between 50 ms and 200 ms, preferably between 65 ms to 100 ms and particularly preferably of 78 ms is preferably selected as the echo time.

Acceleration technology is preferably used to acquire the second diagnostic measurement data. In particular, the use of parallel imaging is conceivable which is preferably used with an acceleration factor of 4 maximum, particularly preferably with an acceleration factor of 3. In particular, the use of Compressed Sensing acceleration technology is conceivable as an alternative or in addition.

The aforementioned parameters concerning the magnetic resonance sequence to the second diagnostic scan Ma3 are advantageously selected such that the second diagnostic measurement data can be recorded in full with the magnetic resonance sequence used in less than 100 seconds, in particular in less than 80 seconds, advantageously in less than 70 seconds and most advantageously in less than 63 seconds. Second image data reconstructed from the second diagnostic measurement data can be reconstructed and provided for diagnosis immediately after completion of the second diagnostic scan Ma3.

The third measuring block Ba3, in particular the second diagnostic scan Ma3, is preferably independent of the receive unit and can be used with a magnetic resonance device which has a main magnetic field with 3 Tesla. The specified ranges of the areas for parameters which are specified in the description of the third measuring block Ba3 for 3 Tesla and a receive unit with 32 reception channels are typically also applicable to other configurations. If the second diagnostic scan Ma3 is performed with a magnetic resonance device which has a main magnetic field with 1.5 Tesla, in particular the acceleration factor, the high frequency pulse for refocusing, the repetition time and the echo time may change. The repetition time at 1.5 Tesla is preferably 4700 ms and the echo time is preferably 111 ms. A maximum of 3, preferably 2 is used as the acceleration factor and the flip angle produced by the high frequency pulse for refocusing is preferably 180°. The third period can be reduced to less than 60 s as a result.

Measuring Block Ba4

Following the third measuring block Ba3, a fourth measuring block Ba4 starts at a fourth point in time Ta4 during the first head imaging. In the fourth measuring block Ba4, a third diagnostic scan Ma4 takes place during which third diagnostic measurement data is acquired.

The fourth point in time Ta4 in the case shown is 118 s after the starting time Ta1 of the first head imaging. The fourth measuring block Ba4 in the case shown has a fourth period of 96 s. The fourth period is preferably between 70 seconds and 130 seconds, in particular between 80 seconds and 120 seconds, in particular between 90 seconds and 115 seconds. Preferably, the fourth period is included almost in full in the pure measurement period of the third diagnostic scan Ma4. During the fourth measuring block Ba4, if necessary, simultaneously with the recording of the third diagnostic scan Ma4, the first and/or second diagnostic measurement data can be at least partly reconstructed and/or evaluated and/or processed as image data.

Furthermore, in the fourth measuring block Ba4 before the start of the third diagnostic scan Ma4 in preparation for the acquisition of measurement data an adjustment measurement can be performed which, for example, comprises an adjustment of a transmitter and/or receiver voltage of the magnetic resonance device. The adjustment measurement typically lasts 15 seconds maximum, in particular 8 seconds maximum, in particular 5 seconds maximum, in particular 2 seconds maximum. The fourth period is typically extended by the duration of the adjustment measurement if an adjustment measurement is required. Preferably, no adjustment measurement is necessary as the resolution and/or orientation of the third diagnostic scan Ma4 preferably do not differ from the second diagnostic scan Ma3.

A remaining period of the fourth measuring block Ba4 can partly be included in the preparation of the acquisition of the third diagnostic measurement data. For example, based on the positioning data determined in evaluation step Ea1, the recording area and/or the position of the measurement layers and/or the layer orientation for the third diagnostic scan Ma4 can be determined. Preferably, this is unnecessary as the resolution and/or layer orientation of the third diagnostic scan Ma4 preferably do not differ from the second diagnostic scan Ma3. Furthermore, the remaining period of the fourth measuring block Ba4 can be partly included in the evaluation or subsequent processing of the third diagnostic measurement data.

The third diagnostic scan Ma4 is a T2-weighted image of the head with cerebrospinal fluid suppression, in particular with fluid suppression. To acquire the third diagnostic measurement data Ma4, preferably a spin echo magnetic resonance sequence with Inversion Recovery is used which for example, is implemented as a Turbo-spin-Echo (TSE) magnetic resonance sequence with fluid suppression (FLAIR). The acquisition of the recording area for the third diagnostic scan Ma4 preferably takes place two-dimensionally, wherein various measurement layers parallel to each other are recorded. The measurement layers, the layer orientation, the layer thickness, the resolution, the number of voxels, the spatial expansion of the area under examination for the third diagnostic scan Ma4 is preferably in conformity with the second diagnostic scan Ma3. A range of between 0.6 mm and 1.2 mm and particularly preferably 0.9 mm has proved suitable as a pixel resolution in a measurement layer (in-plane resolution). The layer thickness of the third diagnostic scan Ma4 is preferably selected between 3 mm and 7 mm, preferably between 4 mm and 6 mm and particularly preferably 5 mm. The measurement layers have a second layer orientation. The second layer orientation is preferably perpendicular to the first layer orientation and a transverse orientation.

The distance between two adjacent measurement layers is preferably between 0% and 50% of the layer thickness, preferably between 10% and 30% of the layer thickness and particularly preferably 20% of the layer thickness. Typically, between 10 and 40 measurement layers, preferably between 20 and 30 measurement layers and particularly preferably 25 measurement layers are acquired. The recording area of the third diagnostic scan Ma4 is preferably a volume which has a spatial expansion in the range of between 100 mm and 200 mm, preferably between 120 mm and 180 mm and particularly preferably between 140 mm and 160 mm perpendicular to a measurement layer. The recording area of the third diagnostic scan Ma4 is preferably a volume which has a spatial expansion in the range of between 150 mm and 300 mm, preferably between 200 mm and 240 mm and particularly preferably of 220 mm in a measurement layer in a first direction. The recording area of the third diagnostic scan Ma4 preferably has a spatial expansion in the range of between 150 mm and 230 mm, preferably between 170 mm and 210 mm and particularly preferably between 185 mm and 195 mm in a second direction perpendicular to the first direction. The spatial expansion in the second direction is preferably less than the spatial expansion in the first direction. Frequency coding is preferably used for spatial encoding of the first direction and phase coding is preferably used for spatial encoding of the second direction. The second direction is preferably a lateral direction.

The number of voxels per measurement layer in the first direction is preferably between 128 and 512 and particularly preferably between 200 and 300, preferably 256. The number of voxels per measurement layer in the second direction is preferably selected such that a second ratio between the spatial expansion in the second direction and the number of voxels in the second direction corresponds to a maximum of the first ratio of the spatial expansion in the first direction and the number of voxels in the first direction. The second ratio is preferably between 80% and 100%, preferably between 95% and 100% of the first ratio. The bandwidth of the frequency coding for the third diagnostic scan Ma4 is typically in the range of between 240 Hertz per pixel and 340 Hertz per pixel, preferably between 270 Hertz per pixel and 310 Hertz per pixel.

A high frequency pulse which is used for refocusing of nuclear spins in the context of the third diagnostic scan Ma4 preferably produces a defined flip angle between 100° and 180° and particularly preferably between 130° and 160°, preferably of 150°. A period in the range of between 5000 ms and 10000 ms, preferably between 6000 ms and 9000 ms and particularly preferably of 8000 ms is preferably selected as the repetition time. A period in the range of between 50 ms and 200 ms, preferably between 100 ms to 140 ms and particularly preferably of 119 ms is preferably selected as the echo time.

For cerebrospinal fluid suppression, in particular for fluid suppression, a high frequency pulse is typically used to invert the nuclear spins of the resonantly excited atoms which typically produces a flip angle of 180°. The high frequency pulse for inversion is typically output before an excitation pulse of the magnetic resonance sequence, wherein the period between the two pulses is described as the inversion time. The inversion time is preferably between 2000 ms and 2600 ms and particularly preferably between 2300 ms and 2450 ms and particularly preferably between 2350 ms and 2400 ms.

Acceleration technology is preferably used to acquire the third diagnostic measurement data. In particular, the use of parallel imaging is conceivable, which is preferably used with an acceleration factor of 4 maximum, in particular preferably with an acceleration factor of 2. In particular, the use of Compressed Sensing acceleration technology is conceivable in turn.

The aforementioned parameters regarding the magnetic resonance sequence to the third diagnostic scan Ma4 are advantageously selected such that the third diagnostic measurement data in less than 130 seconds, in particular in less than 120 seconds, advantageously in less than 100 seconds, most advantageously in less than 97 seconds, can be recorded in full with the magnetic resonance sequence used. Reconstructed image data can be reconstructed from the third diagnostic measurement data and provided for diagnosis immediately after completion of the third diagnostic scan Ma4.

The fourth measuring block Ba4, in particular the third diagnostic scan Ma4, is dependent on the receive unit and the strength of the main magnetic field of the magnetic resonance device. The specified ranges of the areas for parameters which are specified in the description of the fourth measuring block Ba4 for 3 Tesla and a receive unit with 32 reception channels are typically also applicable to other configurations. The aforementioned embodiment of the third diagnostic scan Ma4 is preferably used at 3 Tesla and with a receive unit with 32 reception channels. If fewer than 32 receive channels are used, phase oversampling is preferably increased. For 20 reception channels, phase oversampling of 25% is preferably used and for 16 reception channels, phase oversampling of 48% is preferably used whereby the fourth period increases to 112 s and 128 s. If a receive unit with 64 reception channels is used at 3 Tesla, an acceleration factor of 4 maximum, preferably 3 can be used whereby the fourth period can be reduced to less than 85 s.

If the third diagnostic scan Ma4 is performed with a magnetic resonance device with a main magnetic field with a strength of 1.5 Tesla, the following parameters preferably change:

the repetition time is preferably between 4000 ms and 7000 ms and particularly preferably between 5000 ms and 6000 ms, most preferably 5500 ms the echo time is preferably between 60 ms and 100 ms and particularly preferably between 75 ms and 80 ms the inversion time is preferably between 1800 ms and 2100 ms, preferably between 1900 ms and 2000 ms, in particular preferably 1930 ms a high frequency pulse for refocusing of nuclear spins preferably produces a defined flip angle of 180° preferably no acceleration technology is used the resulting fourth period is typically between 110 s and 140 s, preferably between 120 s and 130 s.

Measuring Block Ba5

Following the fourth measuring block Ba4, a fifth measuring block Ba5 starts at a fifth point in time Ta5 during the first head imaging. In the fifth measuring block Ba5 a fourth diagnostic scan Ma5 takes place during which fourth diagnostic measurement data is acquired.

The fifth point in time Ta5 in the case shown is 214 s after the starting time Ta1 of the first head imaging. The fifth measuring block Ba5 in the case shown has a fifth period of 80 s. The fifth period is preferably between 50 seconds and 110 seconds, in particular between 60 seconds and 100 seconds, in particular between 70 seconds and 90 seconds. Preferably, the fifth period is included almost in full in the pure measurement period of the fourth diagnostic scan Ma5. During the fifth measuring block Ba5, if necessary, simultaneously with the recording of the fourth diagnostic scan Ma5, the first and/or second and/or third diagnostic measurement data can be at least partly reconstructed and/or evaluated and/or processed as image data.

Furthermore, in the fifth measuring block Ba5 before the start of the fourth diagnostic scan Ma5 in preparation for the acquisition of the measurement data, an adjustment measurement can be performed which, for example, comprises an adjustment of a transmitter and/or receiver voltage of the magnetic resonance device. The adjustment measurement typically lasts 15 seconds maximum, in particular 8 seconds maximum, in particular 5 seconds maximum, in particular 2 seconds maximum. If an adjustment measurement is required, the fifth period is typically extended by the duration of the adjustment measurement. Preferably, no adjustment measurement is necessary as the layer orientation of the fourth diagnostic scan Ma5 preferably does not differ from the third diagnostic scan Ma4.

A remaining period of the fifth measuring block Ba5 can partly be included in the preparation of the acquisition of the fourth diagnostic measurement data. For example, based on the positioning data determined in evaluation step Ea1, the recording area and/or the position of the measurement layers and/or the layer orientation for the fourth diagnostic scan Ma5 are determined. The remaining period of the fourth measuring block Ba4 can furthermore be partly included in an evaluation or subsequent processing of the fourth diagnostic measurement data.

The fourth diagnostic scan Ma5 is a diffusion-weighted image of the head. To acquire the fourth diagnostic measurement data Ma5, preferably a gradient echo magnetic resonance sequence is used which, for example, is implemented as an Echoplanar (EPI) magnetic resonance sequence. The fourth diagnostic measurement data is recorded with fat saturation. The acquisition of the recording area for the fourth diagnostic scan Ma5 preferably takes place two-dimensionally, wherein a number of measurement layers parallel to each other are recorded. The layer orientation for the fourth diagnostic scan Ma5 is preferably in conformity with the third diagnostic scan Ma4. A range of between 1.2 mm and 1.8 mm and particularly preferably 1.5 mm has proved suitable as the pixel resolution in a measurement layer (in-plane resolution). Selection of the layer thickness of the fourth diagnostic scan Ma5 is preferably between 3 mm and 7 mm, preferably between 4 mm and 6 mm and particularly preferably 5 mm. The measurement layers have a second layer orientation. The second layer orientation is preferably perpendicular to the first layer orientation and a transverse orientation.

The distance between two adjacent measurement layers is preferably between 0% and 40% of the layer thickness, preferably between 5% and 20% of the layer thickness, preferably between 10% and 15% of the layer thickness and particularly preferably 12% of the layer thickness. Typically, between 15 and 50 measurement layers, preferably between 25 and 40 measurement layers and particularly preferably 31 measurement layers are acquired. The recording area of the fourth diagnostic scan Ma5 is preferably a volume which has a spatial expansion in the range of between 130 mm and 220 mm, preferably between 150 mm and 200 mm and particularly preferably between 170 mm and 180 mm perpendicular to a measurement layer. The recording area of the fourth diagnostic scan Ma5 is preferably a volume which has a spatial expansion in the range of between 170 mm and 300 mm, preferably between 210 mm and 270 mm and particularly preferably of 240 mm in a measurement layer in a first direction. The recording area of the fourth diagnostic scan Ma5 preferably has a spatial expansion in the range of between 170 mm and 300 mm, preferably between 210 mm and 270 mm and particularly preferably between 235 mm and 245 mm in a second direction perpendicular to the first direction. Frequency coding is preferably used for spatial encoding of the first direction and phase coding is preferably used for spatial encoding of the second direction. The second direction preferably connects an anterior and a posterior position of the head of the examination object.

The number of voxels per measurement layer in the first direction is preferably between 128 and 256 and particularly preferably 160. The number of voxels per measurement layer in the second direction preferably corresponds to the number of voxels in the first direction. Interpolation of the voxels or zero-filling of the k-space can take place so that the interpolated voxels in the first direction and in the second direction are the same size. A period in the range of between 2000 ms and 6000 ms, preferably between 3000 ms and 5000 ms and particularly preferably of 4000 ms is preferably selected as the repetition time. A period in the range of between 40 ms and 90 ms, preferably between 55 ms to 75 ms and particularly preferably of 65 ms is preferably selected as the echo time. The bandwidth of the frequency coding for the fourth diagnostic scan Ma5 is typically in the range of between 900 Hertz per pixel and 1500 Hertz per pixel, preferably between 1100 Hertz per pixel and 1300 Hertz per pixel.

Acceleration technology is preferably used to acquire the fourth diagnostic measurement data. In particular, the use of parallel imaging is conceivable which is preferably used with an acceleration factor of between 2 and 4, in particular preferably with an acceleration factor of 3. Furthermore, to acquire the fourth diagnostic measurement data a partial Fourier technique is used to accelerate acquisition, which partial Fourier technique provides that the k-space is only partially sampled, typically 6/8. In particular, the use of Compressed Sensing acceleration technology is conceivable in turn.

For diffusion weighting, a monopolar diffusion diagram is used for the acquisition of the fourth diagnostic measurement data, wherein 6 diffusion weightings maximum, preferably 4 diffusion weightings maximum and particularly preferably 2 diffusion weightings are undertaken. A first diffusion weighting of the diffusion weightings takes place with a first b-value and a second diffusion weighting of the diffusion weightings takes place with a second b-value. The first b-value is preferably 0 $S/mm^2$ and the second b-value is between 500 $S/mm^2$ and 1300 $S/mm^2$, preferably between 700 $S/mm^2$ and 900 $S/mm^2$, in particular preferably 800 $S/mm^2$. A diffusion weighting takes place in a maximum of 15 different directions, preferably in a maximum of 12 different directions and particularly preferably in a maximum of 6 directions, in particular preferably in a maximum of 3 different directions. The diffusion weighting is preferably performed with the TRACE method.

The aforementioned parameters regarding the magnetic resonance sequence for the fourth diagnostic scan Ma5 are advantageously selected such that the fourth diagnostic measurement data can be recorded in full in less than 100 seconds, in particular in less than 90 seconds, advantageously in less than 81 seconds with the magnetic resonance sequence used. Fourth image data reconstructed from the fourth diagnostic measurement data can be reconstructed and provided for diagnosis immediately after completion of the fourth diagnostic scan Ma5.

The fifth measuring block Ba5, in particular the fourth diagnostic scan Ma5, is dependent on the receive unit and the strength of the main magnetic field of the magnetic resonance device. The specified ranges of the areas for parameters which are specified in the description of the fifth measuring block Ba5 for 3 Tesla and a receive unit with 32 reception channels are typically also applicable to other configurations. The aforementioned embodiment of the third diagnostic scan Ma4 is preferably used at 3 Tesla and with a receive unit with 32 or 64 reception channels. If fewer than 32 receive channels are used, the echo time and the repetition time is preferably increased and the acceleration factor reduced. Thus, with 16 or 20 reception channels a repetition time of 4200 ms, an echo time of 72 ms and an acceleration factor of 2 is preferably selected whereby the fifth period is between 75 s and 80 s.

If the fourth diagnostic scan Ma5 is performed with a magnetic resonance device with a main magnetic field with a strength of 1.5 Tesla, the echo time and the repetition time is preferably increased and the acceleration factor reduced. Thus, with 1.5 Tesla and 16 or 20 reception channels, a repetition time of 4500 ms, an echo time of 77 ms and an acceleration factor of 2 is preferably selected whereby the fifth period is between 80 s and 85 s.

Measuring Block Ba6

Following the fifth measuring block Ba5, a sixth measuring block Ba6 starts at a sixth point in time Ta6 during the first head imaging. In the sixth measuring block Ba6, a fifth diagnostic scan Ma6 takes place during which diagnostic measurement data is acquired.

The sixth point in time Ta6 in the case shown is 294 s after the starting time Ta1 of the first head imaging. The sixth measuring block Ba6 in the case shown has a sixth period of 6 s. The sixth period is preferably between 2 seconds and 10 seconds, in particular between 4 seconds and 8 seconds. Preferably, the sixth period is included almost in full in the pure measurement period of the fifth diagnostic scan Ma6. During the sixth measuring block Ba6, if necessary simultaneously with the recording of the fifth diagnostic scan Ma6, the first and/or second and/or third and/or fourth diagnostic measurement data can be at least partly reconstructed and/or evaluated and/or processed as image data.

Furthermore, in the sixth measuring block Ba6 before the start of the fifth diagnostic scan Ma6 in preparation for the acquisition of measurement data, an adjustment measurement, for example, comprising an adjustment of a transmitter and/or receiver voltage of the magnetic resonance device, can be performed. The adjustment measurement typically lasts 15 seconds maximum, in particular 8 seconds maximum, in particular 5 seconds maximum, in particular 2 seconds maximum. If an adjustment measurement is required, the sixth period is typically extended by the duration of the adjustment measurement. Preferably, no adjustment measurement is necessary as the resolution and/or orientation of the fifth diagnostic scan Ma6 preferably do not differ from the third diagnostic scan Ma4.

A remaining period of the sixth measuring block Ba6 can be partly included in the preparation of the acquisition of the fifth diagnostic measurement data. For example, based on the positioning data determined in evaluation step Ea1, the recording area and/or the position of the measurement layers and/or the layer orientation for the fifth diagnostic scan Ma6 can be determined. The remaining period of the sixth measuring block Ba6 can furthermore be partly included in an evaluation or subsequent processing of the fifth diagnostic measurement data.

The fifth diagnostic scan Ma6 is a susceptibility-weighted image of the head. To acquire the fifth diagnostic measurement data Ma6, a gradient echo magnetic resonance sequence is preferably used which, for example, is implemented as an Echoplanar (EPI) magnetic resonance sequence. The fifth diagnostic measurement data is recorded such that the fifth diagnostic measurement data can be reconstructed as fifth image data and the fifth image data indicates a susceptibility of the tissue of the head of the examination object in a spatial distribution. The fifth diagnostic measurement data is recorded with fat saturation.

The acquisition of the recording area for the fifth diagnostic scan Ma6 preferably takes place two-dimensionally, wherein a number of measurement layers parallel to each other are recorded. The measurement layers, the layer orientation, the layer thickness, the resolution, and/or the spatial expansion of the area under examination in at least one direction is preferably in conformity with the second diagnostic scan Ma3 for the fifth diagnostic scan Ma6. A range of between 0.6 mm and 1.2 mm and particularly preferably 0.9 mm has proved appropriate as the pixel resolution in a measurement layer (in-plane resolution). Selection of the layer thickness of the fifth diagnostic scan Ma6 is preferably between 3 mm and 7 mm, preferably between 4 mm and 6 mm and particularly preferably 5 mm. The measurement layers have a second layer orientation.

The second layer orientation is preferably perpendicular to the first layer orientation and a transverse orientation.

The distance between two adjacent measurement layers is preferably between 0% and 50% of the layer thickness, preferably between 10% and 30% of the layer thickness and particularly preferably 20% of the layer thickness. Typically, between 10 and 40 measurement layers, preferably between 20 and 30 measurement layers and particularly preferably 25 measurement layers are acquired. The recording area of the fifth diagnostic scan Ma6 is preferably a volume which has a spatial expansion in the range of between 100 mm and 200 mm, preferably between 120 mm and 180 mm and particularly preferably between 140 mm and 160 mm perpendicular to a measurement layer. The recording area of the fifth diagnostic scan Ma6 is preferably a volume which has a spatial expansion in the range of between 150 mm and 300 mm, preferably between 200 mm and 240 mm and particularly preferably of 220 mm in a measurement layer in a first direction. The recording area of the fifth diagnostic scan Ma6 preferably has a spatial expansion in the range of between 150 mm and 300 mm, preferably between 200 mm and 240 mm and particularly preferably of 220 mm in a second direction perpendicular to the first direction. The spatial expansion in the second direction preferably corresponds to the spatial expansion in the first direction. Frequency coding is preferably used for spatial encoding of the first direction and phase coding is preferably used for spatial encoding of the second direction. The second direction preferably connects an anterior and a posterior position of the head of the examination object.

The number of voxels per measurement layer in the first direction is preferably between 64 and 256 and particularly preferably 128. The number of voxels per measurement layer in the second direction preferably corresponds to the number of voxels in the first direction. Interpolation of voxels or zero-filling of the k-space can take place so that the interpolated voxels in the first direction and in the second direction are the same size. The bandwidth of the frequency coding for the fifth diagnostic scan Ma6 is typically in the range of between 1200 Hertz per pixel and 1800 Hertz per pixel, preferably between 1400 Hertz per pixel and 1600 Hertz per pixel.

A high frequency pulse which is used to excite nuclear spins in the context of the first diagnostic scan Ma2 preferably produces a defined flip angle of between 60° and 90°, preferably of 90°. A period in the range of between 4000 ms and 10000 ms, preferably between 5000 ms and 7000 ms and particularly preferably between 6000 ms and 6300 ms is preferably selected as the repetition time. A period in the range of between 5 ms and 50 ms, preferably between 15 ms to 40 ms and particularly preferably of 30 ms is preferably selected as the echo time.

Acceleration technology is preferably used to acquire the fifth diagnostic measurement data. To acquire the fifth diagnostic measurement data, a partial Fourier technique is used to accelerate acquisition, which partial Fourier technique provides that the k-space is only partially sampled, typically 6/8. In particular, the use of Compressed Sensing acceleration technology is conceivable in turn.

The aforementioned parameters regarding the magnetic resonance sequence for the fifth diagnostic scan Ma6 are advantageously selected such that the fifth diagnostic measurement data can be recorded in full in less than 10 seconds, in particular in less than 8 seconds, advantageously in less than 6 seconds, with the magnetic resonance sequence used. Fifth image data reconstructed from the fifth diagnostic measurement data can be reconstructed and provided for diagnosis immediately after completion of the fifth diagnostic scan Ma6.

The sixth measuring block Ba6 ends at the seventh point in time Ta7.

The seventh point in time Ta7 thus constitutes an end to the acquisition of the measurement data and an end to the evaluation in the first head imaging shown. The seventh point in time Ta7 thus concludes the first head imaging. The seventh point in time Ta7 in the case shown is 300 s after the starting time Ta1 of the first head imaging.

Ratio of Recording Parameters Between Diagnostic Scans

The magnetic resonance sequences used for the recordings Ma1, Ma2, Ma3, Ma4, Ma5, Ma6 have characteristic properties and/or characteristic dependencies which relate to various parameters. For example, the sampling of the k-space for the recordings Ma1, Ma3, Ma4 takes place in a Cartesian manner, preferably the sampling of the k-space for all the recordings Ma1, Ma2, Ma3, Ma4, Ma5, Ma6 takes place in a Cartesian manner. The diagnostic scans Ma2, Ma3, Ma4, Ma5, Ma6 preferably take place two-dimensionally by way of acquisition of parallel layers. The first overview scan Ma1 preferably takes place three-dimensionally. The in-plane resolution for the diagnostic measurement data which has no diffusion weighting is preferably the same and/or in particular also independent of the layer orientation. If the spatial expansion and/or the in-plane resolution and/or the layer thickness and/or the distance between adjacent measurement layers corresponds for the same layer orientation of different diagnostic recordings, the various diagnostic scans are particularly easily comparable: such diagnostic image data shows the same sections of the area under examination in different contrasts, whereby a tissue and/or an anatomy and/or a pathology can be identified with particular precision.

For a diagnostic scan Ma2, Ma3, Ma4, Ma5, Ma6, if the spatial expansion in the second direction corresponds the spatial expansion in the first direction, the second direction preferably connects an anterior and a posterior position of the head of the examination object. If the spatial expansion in the second direction corresponds to the spatial expansion in the first direction for a diagnostic scan of diagnostic scans Ma2-Ma6, the diagnostic scan is typically based on a gradient echo magnetic resonance sequence, in particular on a FLASH and/or an EPI. This is advantageous as such a magnetic resonance sequence for recording diagnostic measurement data is designed to scan a layer in the k-space particularly quickly, in particular after a single high frequency pulse which is used to excite nuclear spins. By way of the quadratic expansion of a measurement layer, in other words, of a corresponding spatial expansion in the first direction and in the second direction, the efficiency of such a magnetic resonance sequence can be put to particularly good use in recording a large amount of measurement data and thereby increasing the signal-to-noise ratio of the resulting image data.

If the spatial expansion in the second direction is less than the spatial expansion in the first direction for a diagnostic scan of the diagnostic scans Ma2-Ma6, then the diagnostic scan is typically based on a spin echo magnetic resonance sequence, in particular on a TSE. This is advantageous as the period of such a magnetic resonance sequence for recording diagnostic measurement data is determined, in particular, by the number of voxels in the second direction and a reduction in the number of voxels in the second direction can bring about a reduction of the corresponding period. The choice of such a spatial expansion in the second direction results in it being possible to cover the lower spatial expansion of the head of an examination object in the anterior-posterior direction than in the head-foot direction via a correspondingly adjusted recording area. By this means, with full coverage of the examination object in an anterior-posterior direction, fold artifacts can be particularly efficiently avoided and the period reduced.

The resolution of the overview measurement data is preferably isotropic. A layer thickness preferably corresponds to recordings of diagnostic measurement data which are recorded with the same layer orientation. Thereby, the diagnostic measurement data which is recorded with the same layer orientation and same layer thickness are particularly easily comparable. The layer orientation of at least two recordings of the recordings Ma2-Ma6 of the diagnostic measurement data is different. This makes possible at least two different views of the area under examination, these views preferably also having different contrasts.

Diagnostic measurement data which does not have any diffusion weighting are preferably recorded with the same layer thickness, same distance between two adjacent measurement layers and/or same in-plane resolution. At least two, preferably at least three of the five diagnostic scans Ma2, Ma3, Ma4, Ma5, Ma6 have the same number of voxels per layer in at least one direction, in particular in the first direction. The spatial expansion in at least one direction, in particular in the first direction, preferably corresponds to at least two, in particular to at least three, preferably to at least four of the five diagnostic scans Ma2, Ma3, Ma4, Ma5, Ma6. Such diagnostic measurement data is particularly easily comparable.

For the fourth diagnostic scan Ma5, in other words, for the diffusion-weighted recording, the number of voxels in one direction is preferably less than for at least one of the diagnostic scans Ma2, Ma3, Ma4. By reducing the number of voxels, for example, the period which is necessary for the fourth diagnostic scan Ma5 can be reduced which, in particular, is efficient for diffusion-weighted recording as the corresponding magnetic resonance sequence has modules for fat saturation and/or diffusion weighting. The number of measurement layers for the fourth diagnostic scan Ma5 is preferably greater than for at least one of the diagnostic scans Ma2, Ma3, Ma4, Ma6. The distance between two adjacent measurement layers for the fourth diagnostic scan Ma5 is preferably less than for at least one of the diagnostic scans Ma2, Ma3, Ma4, Ma6. This is particularly advantageous as compared to the diagnostic scans Ma2, Ma3, Ma4, Ma6, the diffusion-weighted fourth diagnostic scan Mb5 thus exhibits a continuous transition between adjacent layers, whereby an ADC card and/or a TRACE image can be determined with particular precision.

For the fifth diagnostic scan Ma6, the number of voxels in one direction is preferably less than for at least one of the diagnostic scans Ma2, Ma3, Ma4, Ma5. Thereby, the k-space can be scanned particularly quickly, whereby in particular for an EPI-based magnetic resonance sequence, the signal intensity can be improved and/or a largely constant contrast achieved during scanning.

Diagnostic measurement data is preferably recorded such that the spatial expansion in at least one direction, in particular in the first direction, is greater for the fourth diagnostic scan Ma5, in other words, the diagnostic scan with diffusion weighting, than for another diagnostic scan Ma2, Ma3, Ma4, Ma6. Thereby, in particular, for diagnostic scanning with diffusion weighting the signal-to-noise ratio can be increased, which is particularly advantageous for diagnostic scanning with diffusion weighting as the modules for fat saturation and/or diffusion weighting reduce the signal-to-noise ratio.

Preferably, a T1-weighted recording Ma2 has a layer orientation auf which differs from at least one layer orientation of the recordings Ma3, Ma4, Ma5, Ma6. Preferably, the diagnostic scans Ma2, Ma3, Ma4, Ma5, Ma6 each have different contrasts from each other. Preferably, at least one of the diagnostic scans Ma2-Ma6 has a T1 contrast, preferably at least one of the diagnostic scans Ma2-Ma6 has a T2 contrast, preferably at least one of the diagnostic scans Ma2-Ma6 has a FLAIR contrast, preferably at least one of the diagnostic scans Ma2-Ma6 has a susceptibility contrast, and preferably at least one of the diagnostic scans Ma2-Ma6 has a diffusion-weighted contrast. Typically, the signal intensity depends on the underlying tissue and the contrast of the recording, so that different tissues are depicted differently with different contrasts, whereby a tissue particularly can be determined particularly precisely and therefore a pathology particularly precisely detected. With the reconstruction of the diagnostic measurement data to diagnostic image data, the diagnostic image data displays the contrast of the diagnostic measurement data. The aforementioned contrasts in particular enable a comprehensive diagnosis of different clinical pictures, in particular of the aforementioned diseases in the section "General information about the first head imaging".

Preferably, at least two of the five diagnostic scans Ma2, Ma3, Ma4, Ma5, Ma6 are recorded by way of spin echo magnetic resonance sequences. The high frequency pulse which is used for refocusing nuclear spins in the context of the spin echo magnetic resonance sequence is preferably less than 180°, in particular preferably less than 155°. The advantage of such a choice of high-frequency pulse for refocusing is that the SAR burden on the patient caused by the high-frequency pulse for refocusing is reduced, whereby the entire SAR burden on the patient can be reduced for the output of the magnetic resonance sequence and/or the frequency of the high-frequency pulse for refocusing can be increased, whereby the period of the diagnostic scan can be reduced.

Preferably, at least two, in particular preferably at least three, of the five diagnostic scans Ma2, Ma3, Ma4, Ma5, Ma6 are recorded by way of the gradient echo magnetic resonance sequences. Preferably, two of the five diagnostic scans Ma2, Ma3, Ma4, Ma5, Ma6 are recorded by way of an EPI magnetic resonance sequence. Preferably, the measurement data recorded with an EPI magnetic resonance sequence is recorded with fat saturation. A combination of a module for fat saturation with a particularly fast magnetic resonance sequence such as, for example, an EPI-based magnetic resonance sequence, and/or with a magnetic resonance sequence with a particularly small number of high-frequency pulses and therefore with a particularly low SAR load for the examination object such as, for example, a gradient echo-based magnetic resonance sequence is particularly advantageous as a module comprising a magnetic resonance sequence for fat saturation especially increases the period of a magnetic resonance sequence and/or the SAR load for the examination object.

Preferably, the measurement data recorded with an EPI magnetic resonance sequence is recorded with an echo time, which echo time particularly preferably does not exceed the minimum echo time by 20% maximum, preferably by 10% maximum. Thereby, the period of the corresponding measuring block and/or the first imaging period can be reduced. The high frequency pulse which is used to excite nuclear spins in the context of the gradient magnetic resonance sequence is preferably between 80° and 90°. A particularly high signal can be produced by this means. Phase oversampling is preferably omitted for a recording with an EPI magnetic resonance sequence. Thereby the period of the corresponding measuring block and/or the first imaging period can be reduced.

The bandwidth of the frequency coding for the fourth and for the fifth diagnostic scan Ma5, Ma6 is typically wider than 1000 Hertz per pixel and preferably wider than 1200 Hertz per pixel. In particular, rapid scanning of the k-space, a high signal intensity and/or a largely constant contrast during scanning can be ensured thereby for EPI-based magnetic resonance sequences. The lower signal-to-noise ratio produced by the high bandwidth of the frequency coding can be compensated by a higher number of recorded points in the k-space with such magnetic resonance sequences, whereby the function of the EPI-based magnetic resonance sequences can be utilized particularly well by the high bandwidth of the frequency coding. In addition, particularly due to movement, artifacts can be reduced. The bandwidth of the frequency coding for the second and for the third diagnostic scan Ma3, Ma4 is typically in the range of between 100 Hertz per pixel and 500 Hertz per pixel, preferably in the range of between 200 Hertz per pixel and 300 Hertz per pixel. In particular, the signal-to-noise ratio can be improved by the choice of such a low bandwidth of frequency coding for spin echo-based magnetic resonance sequences. The bandwidth of the frequency coding is typically smaller for the first, second, and/or third diagnostic scan Ma2, Ma3, Ma4 than for the fourth and/or fifth diagnostic scan Ma5, Ma6. The bandwidth of the frequency coding for the first diagnostic scan Ma2 is typically in the range of between 200 Hertz per pixel and 500 Hertz per pixel, preferably between 300 Hertz per pixel and 400 Hertz per pixel. The bandwidth of the frequency coding for the first diagnostic scan Ma2 is preferably 360 Hertz per pixel. These dependencies of the bandwidth of the frequency coding enable a particularly good signal-to-noise ratio of the diagnostic measurement data, or diagnostic image data, based on which a particularly reliable diagnosis can be made and/or a particularly short first imaging period which is within the aforementioned limits.

The repetition time of the third diagnostic scan Ma4 is preferably longer than the repetition time of the second diagnostic scan Ma3. The echo time of the third diagnostic scan Ma4 is preferably longer than the echo time of the second diagnostic scan Ma4. The repetition time of the fifth diagnostic scan Ma6 is preferably longer than the repetition time of the fourth diagnostic scan Ma5. The echo time of the fourth diagnostic scan Ma5 is preferably longer than the echo time of the fifth diagnostic scan Ma6. These dependencies of the repetition times and/or echo times enable particularly advantageous contrasts of the diagnostic measurement data, or diagnostic image data, based on which a particularly reliable diagnosis can be made and/or a particularly short first imaging period which is within the aforementioned limits.

Temporal Sequence of the Diagnostic Scans

The first head imaging is characterized in that a maximum of one first user interaction Ia1 is necessary at the start of the first head imaging. The subsequent measuring blocks Ba2, Ba3, Ba4, Ba5, Ba6 take place automatically, enabling the user to monitor the embodiment of the methods, for example. The temporal sequence of the measuring blocks Ba2, Ba3, Ba4, Ba5, Ba6 can be selected as required. The sequence of the measuring blocks Ba2-Ba6 is preferably selected such that the measurement data recorded via the measuring blocks Ba2-Ba6 and image data that can be reconstructed from it is in descending order of importance for the user. Thus, measurement data of particular relevance for a diagnosis can be recorded at an earlier time at which the patient is more cooperative and/or the probability of the patient moving is lower, whereby the quality of the diagnostic measurement data can be increased. The sequence of the measuring blocks Ba2-Ba6 is preferably selected such that diagnostic scans of consistent orientation can be combined in one block and the at least two blocks are executed one after the other. Thereby the probability of the patient moving between two diagnostic scans of the same orientation, in other words, two diagnostic scans of the same block, is reduced, whereby the two diagnostic scans of the same orientation can be better compared with each other and in particular also depicted superimposed and/or a subtraction can be performed. The sequence of the blocks and/or the sequence of the diagnostic scans within a block can be selected as required. It is thereby possible to individually adjust the sequence to the requirements of the user.

Ratio of the Periods Between the Diagnostic Scans and the Overview Scan

The period of the fourth measuring block Ba4 is typically longer than the period of the fifth measuring block Ba5. The period of the fifth measuring block Ba5 is typically longer than the period of the third measuring block Ba3. The period of the third measuring block Ba3 is typically longer than the period of the second measuring block Ba2. The period of the second measuring block Ba2 is typically longer than the period of the sixth measuring block Ba6.

The period of the first measuring block Ba1 and of the sixth measuring block Ba6 combined is preferably shorter than the period of the second measuring block Ba2. The period of the first measuring block Ba1 and of the second measuring block Ba2 combined is preferably shorter than the period of the third measuring block Ba3. The period of the first measuring block Ba1 and of the second measuring block Ba2 and of the sixth measuring block Ba6 combined is preferably shorter than the period of the third measuring block Ba3. The period of the first measuring block Ba1 and of the second measuring block Ba2 and of the sixth measuring block Ba6 combined is preferably shorter than the period of the fourth measuring block Ba4 or of the fifth measuring block Ba5. The period of the third measuring block Ba3 and of the sixth measuring block Ba6 combined is preferably shorter than the period of the fourth measuring block Ba4 or of the fifth measuring block Ba5. The period of the first measuring block Ba1, of the second measuring block Ba2, of the sixth measuring block Ba6 and of the third measuring block Ba3 combined is preferably shorter than the total of the period of the fourth measuring block Ba4 and the period of the fifth measuring block Ba5.

The two measuring blocks lasting the longest are preferably structured such that the recording of the corresponding measurement data takes place with fat saturation. This is particularly advantageous as a magnetic resonance sequence with a module for fat saturation typically lasts longer than a magnetic resonance sequence without a module for fat saturation. The sixth and last measuring block Ba6 preferably has a particularly short sixth period, wherein the fifth diagnostic scan Ma6 of the sixth measuring block Ba6 takes place with a contrast which immediately depicts physical properties, in particular the susceptibility, of the tissue in the area under examination. For the fifth diagnostic scan Ma6, a magnetic resonance sequence was selected such that the physical property can be detected immediately in a particularly short period.

The fourth diagnostic scan Ma5 which has a diffusion weighting, typically requires at least one module for fat saturation and one module for diffusion weighting, whereby for this reason the fifth period Ta5 is typically at least two modules longer than one period of a measuring block which has one or none of the modules and is based on the same magnetic resonance sequence as the fourth diagnostic scan Ma5. Nevertheless, in order to keep the fifth period Ta5 as short as possible, the fourth diagnostic scan Ma5 is performed with an EPI-based magnetic resonance sequence. EPI-based magnetic resonance sequences are characterized by a short period.

The period of a measuring block typically comprises the recording period of the measuring block and if applicable, a period of reconstruction, insofar as the reconstruction of the measurement data is performed within the measuring block which may, in particular, be applicable to overview measurement data. The reconstruction period of the overview measurement data is typically 20% maximum, preferably 10% maximum and particularly preferably 5% maximum of the recording period of the overview measurement data Ma1. The period of the reconstruction diagnostic measurement data is typically at least 1 s and/or 10% maximum, preferably 5% maximum and particularly preferably 3% maximum of the recording period of the diagnostic measurement data Ma2-Ma6.

FIG. 2—Second Head Imaging

General Information about the Second Head Imaging

The first head imaging, the sequence of which is shown in FIG. 1, in particular provides diagnostic measurement data which can serve as the basis for an assessment of the anatomy and/or pathology of the head of the examination object. In addition, the second head imaging provides diagnostic measurement data which enables a comprehensive diagnosis of the head as, in particular, tumors, neoplasms, inflammation, infections and vascular diseases can be diagnosed. In particular, the second head imaging can serve as the basis for the diagnosis of a stenosis and/or a stroke as, for example, perfusion, microlesions, internal bleeding and/or calcifications can be detected in vessels by way of the additional measurement data. In particular, small intracerebral hemorrhages can be detected by way of the second head imaging. In addition, the second head imaging provides further diagnostic measurement data on the basis of which White Matter (WM) and Gray Matter (GM) can be distinguished particularly well. As in the first head imaging, in particular, it is an aim of the second head imaging to record the diagnostic measurement data required for the assessment of the anatomy and/or pathology of the head of the examination object in a short second imaging period, compared with traditional comparable examinations of the head via a magnetic resonance device. The diagnostic measurement data is preferably recorded in the short second imaging period such that sufficiently high-quality image data can be ascertained and provided as the basis for a diagnosis of the head despite the comparatively short second imaging period.

The second head imaging has a second imaging period which is from a starting time Tb1 of the second head imaging to a tenth point in time Tb10, at which the recording of measurement data in the second head imaging is completed. If the second head imaging is performed via a magnetic resonance device with a main magnetic field with a strength of 1.5 Tesla, the second imaging period preferably lasts a maximum of 19 minutes. If the second head imaging is performed via a magnetic resonance device with a main magnetic field with a strength of 3 Tesla, the second imaging period advantageously lasts a maximum of 15 minutes, in particular advantageously a maximum of 12 minutes, particularly advantageously a maximum of 10.5 minutes and most advantageously a maximum of 10 minutes. If a maximum imaging period is established, the user has planning security for the period and/or feasibility of the second head imaging.

The second imaging period is, in particular, dependent on the choice of receive unit which is used to receive magnetic resonance signals. The higher the number of individual receive channels the receive unit has, the shorter the second imaging period can be. A variability of the second imaging period is, in particular, analogous to the specified areas, or to the variability for the periods of the measuring blocks comprising the second imaging. The second imaging period is, in particular, arranged as a maximum imaging period which ideally is not exceeded for the performance of the second head. A period of user interactions or parameter settings for the acquisition of measurement data can be included in the second imaging period. In certain cases, it is also conceivable that a period of patient positioning is included in the second imaging period. Alternatively, the second imaging period can also be characterized in that more than 60 percent, in particular more than 75 percent, most advantageously more than 90 percent of a series of several examinations in the clinical routine which are performed in accordance with the diagram shown in FIG. 2 for the second head imaging include the second imaging period.

FIG. 2 shows a particularly advantageous case in which the second imaging period of the second head imaging lasts less than 10.5 minutes. After recording of the measurement data has been completed in the second head imaging, further time may elapse in which subsequent processing and/or evaluation of the measurement data takes place. However, the examination object must only remain in the magnetic resonance device during the second imaging period. After the second imaging period, the next examination object can be positioned in the magnetic resonance device, whereby better utilization of the device is achieved.

Description of a Possible Concrete Sequence of the Second Head Imaging

Preparation of the Second Head Imaging

The preparation of the second head imaging may in principle comprise some or all the elements already described for the preparation of the first head imaging. Therefore, with regard to the description of the preparation of the second head imaging, please refer to the description of the preparation of the first head imaging.

In addition to the preparation of the first head imaging, preparation of the administration of the contrast agent Cb takes place in the preparation of the second head imaging. The administration of contrast agent Cb for the second head imaging takes place during the measuring procedure of the second head imaging. In the case shown in FIG. 2, the administration of contrast agent Cb takes place immediately before the start of the sixth measuring block Bb6 of the second head imaging. The preparation of the administration of contrast agent may, for example, comprise an injection of a needle into the examination object, via which a magnetic resonance contrast agent can be administered during the measurement procedure. Common magnetic resonance contrast agents, such as gadolinium, for example, Gd-DTPA, can be used for this.

Sequence of the Measuring Blocks

The measuring block Bb1 of the second head imaging is analogous to the measuring block Ba1 of the first head imaging. The measuring block Bb2 of the second head imaging is analogous to the measuring block Ba2 of the first head imaging. The measuring block Bb3 of the second head imaging is analogous to the measuring block Ba4 of the first head imaging. The measuring block Bb6 of the second head imaging comprises a recording Mb6 which is analogous to the fourth diagnostic scan Mb5 of the measuring block Ba5 of the first head imaging. The measuring block Bb7 of the second head imaging is analogous to the measuring block Ba3 of the first head imaging. Therefore, reference is made to the description of the corresponding measuring blocks in the first head imaging for the description of the measuring blocks Bb1, Bb2, Bb3, Bb6, Bb7. Likewise, for the ratios of the recording parameters between the diagnostic scans Bb1, Bb2, Bb3, Bb6, Bb7, reference is made to the description of the corresponding measuring blocks in the first head imaging. Likewise, for the ratio of the period between the diagnostic scans Bb1, Bb2, Bb3, Bb6, Bb7 and the overview scan, reference is made to the description of the corresponding measuring blocks in the first head imaging.

The sequence of the nine measuring blocks Bb1, Bb2, Bb3, Bb4, Bb5, Bb6, Bb7, Bb8, Bb9 of the second head imaging is briefly summarized at this point, wherein with regard to further descriptions and alternative expiry options for the measuring blocks Bb1, Bb2, Bb3, Bb6, Bb1, reference is made to the description of the measuring blocks Ba1, Ba2, Ba3, Ba4, Ba5 in FIG. 1. The measuring blocks Bb4, Bb5, Bb8, Bb9 are explained in detail. The measuring blocks Ba2, Ba3, Ba4, Ba5 can be performed in any order.

Measuring Block Bb1

The second head imaging shown starts at a first point in time Tb1 or starting time Tb1 with the first measuring block Bb1. In the first measuring block Ba1 a first user interaction Ib1, a first overview scan Mb1, takes place during which first overview measurement data is acquired, and a first evaluation step Eb1 analogous to the first user interaction Ia1, the first overview scan Ma1 and the first evaluation step Ea1, wherein positioning data can be extracted. The positioning data can be provided for the following recordings Mb2, Mb3, Mb4, Mb5, Mb6, Mb7, Mb8, Mb9. Based on the positioning data, further measures can be taken in the context of the first evaluation step Eb1 analogous to the first evaluation step Ea1. The first measuring block Bb1 ends at the point in time Tb2.

Measuring Block Bb2

The second measuring block Bb2 begins at the point in time Tb2. In the second measuring block Bb2 a first diagnostic scan Mb2 takes place which is arranged as a T1-weighted image of the head and corresponds to the first diagnostic scan Ma2 of the first head imaging. The second measuring block Bb2 ends at the point in time Tb3.

Measuring Block Bb3

The third measuring block Bb3 begins at the point in time Tb3. In the third measuring block Bb3 a second diagnostic scan Mb3 takes place which is arranged as a T2-weighted image of the head with cerebrospinal fluid suppression, in particular with fluid suppression, and corresponds to the third diagnostic scan Ma4 of the first head imaging. The third measuring block Bb3 ends at the point in time Tb4. The fourth point in time Tb4 in the case shown is 152 s after the starting time Tb1 of the second head imaging.

Measuring Block Bb4

The fourth measuring block Bb4 begins at the point in time Tb4. In the fourth measuring block Bb4 a third diagnostic scan Mb4 takes place during which third diagnostic measurement data is acquired and which is arranged as a susceptibility-weighted image of the head. The fourth measuring block Bb4 ends at the point in time Tb5. The fifth point in time Tb5 in the case shown is 225 s after the starting time Tb1 of the second head imaging.

The fourth measuring block Bb4 in the case shown has a fourth period of 73 s. The fourth period is preferably between 45 seconds and 110 seconds, in particular between 60 seconds and 95 seconds, in particular preferably between 70 seconds and 80 seconds. Preferably, the fourth period is almost completely included in the pure measurement period of the third diagnostic scan Mb4. During the fourth measuring block Bb4, if necessary, simultaneously with the recording of the third diagnostic scan Mb4, the first and/or second diagnostic measurement data can be at least partly reconstructed and/or evaluated and/or processed as image data.

Furthermore, in the fourth measuring block Bb4 before the start of the third diagnostic scan Mb4 in preparation for the acquisition of the measurement data, an adjustment measurement can be performed which, for example, comprises an adjustment of a transmitter and/or receiver voltage of the magnetic resonance device. The adjustment measurement typically lasts 15 seconds maximum, in particular 8 seconds maximum, in particular 5 seconds maximum, in particular 2 seconds maximum. If an adjustment measurement is required, the fourth period is typically extended by the duration of the adjustment measurement. Preferably, no adjustment measurement is necessary because the resolution and/or orientation of the third diagnostic scan Mb4 preferably do not differ from the second diagnostic scan Mb3.

A remaining period of the fourth measuring block Bb4 can be partly included in the preparation of the acquisition of the third diagnostic measurement data. For example, the recording area and/or the position of the measurement layers and/or the layer orientation for the third diagnostic scan Mb4 can be determined on the basis of the positioning data determined in evaluation step Eb1. Furthermore, the remaining period of the fourth measuring block Bb4 can be partly included in the evaluation or subsequent processing of the third diagnostic measurement data.

The third diagnostic scan Mb4 is arranged as a susceptibility-weighted image of the head. To acquire the third diagnostic measurement data Mb4A a gradient echo magnetic resonance sequence is preferably used which for example, is implemented as a Fast Low-Angle Shot (FLASH) magnetic resonance sequence. The third diagnostic measurement data is recorded such that the third diagnostic measurement data can be reconstructed as third image data and the third image data specifies a susceptibility of the head of the examination object in a spatial distribution.

The acquisition of the recording area for the third diagnostic scan Mb4 preferably takes place two-dimensionally, wherein several measurement layers parallel to each other are recorded. The measurement layers, the layer orientation, the layer thickness, the resolution, and/or the spatial expansion of the area under examination in at least one direction for the third diagnostic scan Ma4 is preferably in conformity with the second diagnostic scan Ma3. A range of between 0.6 mm and 1.2 mm and particularly preferably 0.9 mm, has proved suitable as a pixel resolution in a measurement layer (in-plane resolution). The selection of the layer thickness of the third diagnostic scan Ma4 is preferably between 3 mm and 7 mm, preferably between 4 mm and 6 mm and particularly preferably 5 mm. The measurement layers have a second layer orientation. The second layer orientation is preferably perpendicular to the first layer orientation and a transverse orientation.

The distance between two adjacent measurement layers is preferably between 0% and 50% of the layer thickness, preferably between 10% and 30% of the layer thickness and particularly preferably 20% of the layer thickness. Typically, between 10 and 40 measurement layers, preferably between 20 and 30 measurement layers and particularly preferably 25 measurement layers are acquired. The recording area of the third diagnostic scan Mb4 is preferably a volume which has a spatial expansion in the range of between 100 mm and 200 mm, preferably between 120 mm and 180 mm and particularly preferably between 140 mm and 160 mm perpendicular to a measurement layer.

The recording area of the third diagnostic scan Mb4 is preferably a volume which has a spatial expansion in the range of between 150 mm and 300 mm, preferably between 200 mm and 240 mm and particularly preferably of 220 mm in a measurement layer in a first direction. The recording area of the third diagnostic scan Mb4 preferably has a spatial expansion in the range of between 150 mm and 230 mm, preferably between 170 mm and 210 mm and particularly preferably between 185 mm and 195 mm in a second direction perpendicular to the first direction. Frequency coding is preferably used for spatial encoding of the first direction, and phase coding is preferably used for spatial encoding of the second direction. The second direction is preferably a lateral direction.

The magnetic resonance sequence used to record the third diagnostic scan Mb4 preferably has a module which ensures compensation of a flux in the direction of frequency coding and/or in a third direction which is perpendicular to the first direction and to the second direction. The number of voxels per measurement layer in the first direction is preferably between 128 and 512 and particularly preferably between 200 and 300, preferably 256. The number of voxels per measurement layer in the second direction is preferably selected such that a second ratio between the spatial expansion in the second direction and the number of voxels in the second direction corresponds as a maximum to a first ratio of the spatial expansion in the first direction and the number of voxels in the first direction. The second ratio is preferably between 80% and 100% and preferably between 95% and 100% of the first ratio. Interpolation of the voxels or zero-filling of the k-space can take place so that the interpolated voxels in the first direction and in the second direction are the same size. A high frequency pulse which is used to excite nuclear spins in the context of the third diagnostic scan Mb3 preferably produces a defined flip angle of between 10° and 30° and preferably of 20°.

A period in the range of between 250 ms and 1000 ms, preferably between 400 ms and 800 ms and particularly preferably between 5500 ms and 650 ms is preferably selected as the repetition time. A period in the range of between 5 ms and 50 ms, preferably between 10 ms to 30 ms and particularly preferably of 20 ms is preferably selected as the echo time. Acceleration technology is preferably used to acquire the third diagnostic measurement data Mb4. In particular, the use of parallel imaging is conceivable, which is preferably used with an acceleration factor of 3 maximum and particularly preferably with an acceleration factor of 2. Here too in turn, the use of Compressed Sensing acceleration technology is conceivable. The bandwidth of frequency coding for the third diagnostic scan Mb4 is typically in the range of between 200 Hertz per pixel and 500 Hertz per pixel, preferably between 300 Hertz per pixel and 400 Hertz per pixel.

The aforementioned parameters regarding the magnetic resonance sequence for the third diagnostic scan Mb4 are advantageously selected such that the third diagnostic measurement data can be recorded in full in less than 90 seconds, in particular in less than 80 seconds, advantageously in less than 75 seconds, with the magnetic resonance sequence used.

The fourth measuring block Bb4 of the second head imaging may alternatively also comprise the fifth diagnostic scan Ma6 of the first head imaging as a diagnostic scan, so that the third diagnostic scan Mb4 of the second head imaging corresponds to the fifth diagnostic scan Ma6 of the first head imaging. In this case, the fourth period is reduced accordingly from 73 s to, for example, 6 s. For a comprehensive diagnosis of the head, in particular for the detection of intracerebral hemorrhages, the susceptibility-weighted image of the head based on an EPI is typically preferred. Third image data reconstructed from the third diagnostic measurement data can be reconstructed and provided for diagnosis immediately after completion of the third diagnostic scan Mb4.

The fourth measuring block Bb4, in particular the third diagnostic scan Mb4, is preferably independent of the receive unit and can be used with a magnetic resonance device which has a main magnetic field with 3 Tesla. If the third diagnostic scan Mb4 is performed with a magnetic resonance device which has a main magnetic field with 1.5 Tesla, so in particular the repetition time and the echo time may change. The specified ranges of the areas for parameters which are specified in the description of the fourth measuring block Bb4 for 3 Tesla and a receive unit with 32 reception channels are typically also applicable to other configurations. The repetition time at 1.5 Tesla is preferably 830 ms and the echo time is preferably 25 ms. The fourth period may be increased to 103 s as a result.

Measuring Block Bb5

The fifth measuring block Bb5 begins at the point in time Tb5. In the fifth measuring block Bb5 a fourth diagnostic scan Mb5 takes place which is arranged as a T1-weighted image of the head. The fifth measuring block Bb5 ends at the point in time Tb6. The sixth point in time Tb6 in the case shown is 258 s after the starting time Tb1 of the second head imaging.

The fifth measuring block Bb5 in the case shown has a fifth period of 33 s. The fifth period is preferably between 20 seconds and 45 seconds, in particular between 25 seconds and 40 seconds, in particular preferably between 30 seconds and 35 seconds. Preferably, the fifth period is included almost completely in the pure measurement period of the fourth diagnostic scan Mb5. During the fifth measuring block Bb5, if necessary, simultaneously with the recording of the fourth diagnostic scan Mb5, the first and/or second and/or third diagnostic measurement data can be at least partly reconstructed and/or evaluated and/or processed as image data.

Furthermore, in the fifth measuring block Bb5 before the start of the fourth diagnostic scan Mb5 in preparation for the acquisition of the measurement data, an adjustment measurement can be performed which, for example, comprises an adjustment of a transmitter and/or receiver voltage of the magnetic resonance device. The adjustment measurement typically lasts 15 seconds maximum, in particular 8 seconds maximum, in particular 5 seconds maximum, in particular 2 seconds maximum. The fifth period is typically extended by the duration of the adjustment measurement if an adjustment measurement is required. Preferably, no adjustment measurement is necessary as the resolution and/or orientation of the fourth diagnostic scan Mb5 preferably do not differ from the third diagnostic scan Mb4.

A remaining period of the fifth measuring block Bb5 can be partly included in a preparation of the acquisition of the fourth diagnostic measurement data. For example, the recording area and/or the position of the measurement layers and/or the layer orientation for the fourth diagnostic scan Mb5 can be determined on the basis of the positioning data determined in evaluation step Eb1. Furthermore, the remaining period of the fifth measuring block Bb5 can be partly included in an evaluation or subsequent processing of the fourth diagnostic measurement data.

The fourth diagnostic scan Mb4 is arranged as a T1-weighted image of the head. The acquisition of the fourth diagnostic measurement data Mb4 preferably takes place with the magnetic resonance sequence which is used for the third diagnostic scan, with the following changed parameters:

A high frequency pulse which is used to excite nuclear spins in the context of the fifth diagnostic scan Mb5 preferably produces a defined flip angle of between 70° and 90°, preferably of 80°. A period in the range of between 100 ms and 400 ms, preferably between 200 ms and 300 ms and particularly preferably between 220 ms and 260 ms is preferably selected as the repetition time. Preferably, the measurement data is recorded with an echo time which exceeds the minimum echo time by 20% maximum, preferably by 10% maximum and particularly preferably does not exceed it. A period of less than 5 ms, preferably of less than 4 ms and particularly preferably of less than 3 ms is preferably selected as the echo time. The fifth diagnostic scan Mb5 is preferably free of the module of the fourth diagnostic scan Mb4 which ensures compensation of a flux in the direction of frequency coding and/or in a third direction which is perpendicular to the first direction and to the second direction.

The aforementioned parameters regarding the magnetic resonance sequence for the fourth diagnostic scan Mb5 are advantageously selected such that the fourth diagnostic measurement data can be recorded in full in less than 50 seconds, in particular in less than 40 seconds, advantageously in less than 35 seconds, with the magnetic resonance sequence used. Fourth image data reconstructed from the fourth diagnostic measurement data can be reconstructed and provided for diagnosis immediately after completion of the fourth diagnostic scan Mb5.

The fifth measuring block Bb5, in particular the fourth diagnostic scan Mb5, is preferably independent of the receive unit and can be used with a magnetic resonance device which has a main magnetic field with 3 Tesla. If the fourth diagnostic scan Mb5 is performed with a magnetic resonance device which has a main magnetic field with 1.5 Tesla, a spin echo magnetic resonance sequence is preferably used instead of the gradient echo magnetic resonance sequence. In addition to the underlying magnetic resonance sequence, the following parameters are preferably changed:

the repetition time is preferably between 450 ms and 700 ms and particularly preferably between 550 ms and 570 ms the echo time is preferably between 5 ms and 25 ms and particularly preferably between 10 ms and 15 ms a high frequency pulse to excite nuclear spins preferably produces a defined flip angle of 90° the bandwidth for frequency coding is preferably selected in the range of between 100 Hertz per pixel and 200 Hertz per pixel, preferably 150 Hertz per pixel the second direction, the direction of phase coding, preferably connects an anterior and a posterior position of the head of the examination object the resulting second period is typically between 50 s and 90 s, preferably between 65 s and 75 s.

Measuring Block Bb6

The sixth measuring block Bb6 begins at the point in time Tb6.

In the example shown in FIG. 2, the administration of contrast agent Cb takes place at the start of the sixth measuring block Bb6 at the point in time Tb6. For this, a magnetic resonance contrast agent is administered, in particular injected into the examination object. The administration of contrast agent Cb for the second head imaging advantageously takes place before, at the start of, or during the fifth diagnostic scan Mb6. The administration of contrast agent Cb is preferably automated. The administration of contrast agent Cb can also take place manually or semi-automatically, which may require a second user interaction. The second user interaction may then comprise the administration of contrast agent Cb. In the sixth measuring block Bb6 a fifth diagnostic scan Mb6 takes place which is arranged as a diffusion-weighted image of the head and corresponds to the fourth diagnostic scan Ma5 of the first head imaging. The sixth measuring block Bb6 ends at the point in time Tb7. The seventh point in time Tb7 in the case shown is 338 s after the starting time Tb1 of the second head imaging. The fifth diagnostic scan Mb6 is preferably insensitive to contrast agent.

Measuring Block Bb7

The seventh measuring block Bb7 begins at the point in time Tb7. In the seventh measuring block Bb7 a sixth diagnostic scan Mb7 takes place which is arranged as a T2-weighted image of the head and corresponds to the second diagnostic scan Ma3 of the first head imaging. The seventh measuring block Bb7 ends at the point in time Tb8. The eighth point in time Tb8 in the case shown is 400 s after the starting time Tb1 of the second head imaging. The sixth diagnostic scan Mb7 is preferably insensitive to contrast agent.

Measuring Block Bb8

The eighth measuring block Bb8 begins at the point in time Tb8. The eighth point in time Tb8 in the case shown is 400 s after the starting time Tb1 of the second head imaging. The eighth point in time Tb8 in the case shown is 142 s after the point in time Tb6 at which the administration of the contrast agent Cb takes place. The eighth measuring block Bb8 preferably begins at least 100 s, in particular at least 120 s and particularly preferably at least 140 s after the point in time Tb6 at which the administration of the contrast agent Cb takes place. The eighth measuring block Bb8 ends at the ninth point in time Tb9. The ninth point in time Tb9 in the case shown is 433 s after the starting time Tb1 of the second head imaging.

The eighth measuring block Bb8 preferably begins in the range of between 50 s and 300 s, in particular in the range of between 100 s and 200 s and particularly preferably in the range of between 125 s and 165 s, after the point in time Tb6 at which the administration of the contrast agent Cb takes place. In the eighth measuring block Bb8 a seventh diagnostic scan Mb8 takes place which is arranged as a T1-weighted image of the head and corresponds to the fourth diagnostic scan Mb5 of the second head imaging. Therefore, the seventh diagnostic scan Mb8 preferably only differs from the fourth diagnostic scan Mb5 in that a contrast agent was administered to the examination object before the start of the seventh diagnostic scan Mb8. If, for example, the fourth diagnostic measurement data is reconstructed as fourth image data and the seventh diagnostic measurement data as seventh image data, in a comparison of the fourth image data with the seventh image data, areas in which the contrast agent is concentrated can be identified. Thus, for example, a tumor and/or blood vessels and/or inflammation can be detected. Seventh image data reconstructed from the seventh diagnostic measurement data can be reconstructed and provided for diagnosis immediately after completion of the seventh diagnostic scan Mb8.

Measuring Block Bb9

The ninth measuring block Bb9 begins at the point in time Tb9. The ninth point in time Tb9 in the case shown is 433 s after the starting time Tb1 of the second head imaging. The ninth point in time Tb9 in the case shown is 175 s after the point in time Tb6 at which the administration of the contrast agent Cb takes place. The ninth measuring block Bb9 preferably begins at least 150 s, in particular at least 160 s and particularly preferably at least 170 s after the point in time Tb6 at which the administration of the contrast agent Cb takes place.

In the ninth measuring block Bb9 an eighth diagnostic scan Mb9 takes place which is arranged as a T1-weighted image of the head. The ninth measuring block Bb9 in the case show has a ninth period of 182 s. The ninth period is preferably between 150 seconds and 280 seconds, in particular between 170 seconds and 200 seconds, in particular between 180 seconds and 190 seconds. Preferably, the ninth period is almost completely included in the pure measurement period of the eighth diagnostic scan Mb9. During the ninth measuring block Bb9, if necessary, simultaneously with the recording of eighth diagnostic scan Mb9, diagnostic measurement data recorded previously can be at least partly reconstructed and/or evaluated and/or processed as image data.

Furthermore, in the ninth measuring block Bb9 before the start of the eighth diagnostic scan Mb9 in preparation for the acquisition of the measurement data, an adjustment measurement can be performed which, for example, comprises an adjustment of a transmitter and/or receiver voltage of the magnetic resonance device. The adjustment measurement typically lasts 15 seconds maximum, in particular 8 seconds maximum, in particular 5 seconds maximum, in particular 2 seconds maximum. If an adjustment measurement is required, the ninth period is typically extended by the duration of the adjustment measurement. An adjustment measurement may be necessary as, contrary to the preceding recordings, the eighth diagnostic scan Mb9 typically takes place three-dimensionally and the recording area of the eighth diagnostic scan Mb9 can be distinguished from the preceding recordings in at least one direction. Preferably, an adjustment measurement which also includes the recording area of the eighth diagnostic scan Mb9 was already performed in a preceding measuring block.

A remaining period of the ninth measuring block Bb9 can be partly included in a preparation of the acquisition of the eighth diagnostic measurement data. For example, based on the positioning data determined in evaluation step Eb1, the recording area and/or the position of the measurement layers and/or the layer orientation for the eighth diagnostic scan Mb9 can be determined. Furthermore, the remaining period of the ninth measuring block Bb9 can be partly included in an evaluation or subsequent processing of the eighth diagnostic measurement data.

The eighth diagnostic scan Mb9 is arranged as a three-dimensional image of the head with GM-WM-T1 contrast in which the contrast between Gray Matter and White Matter is greater in comparison to the T1 contrast. To acquire the eighth diagnostic measurement data Mb9, preferably a three-dimensional gradient echo magnetic resonance sequence with preparation of magnetization, in particular with Inversion Recovery which, for example, is implemented as a "Magnetization prepared rapid gradient-echo" (MP-RAGE) magnetic resonance sequence, is used.

To prepare the magnetization, typically a high frequency pulse for inversion of the nuclear spins of the resonantly excited atoms is used, which typically produces a flip angle of 180°. The high frequency pulse for inversion is typically output before an excitation pulse of the magnetic resonance sequence, wherein the period between the two pulses is referred to as the inversion time. The inversion time is preferably between 900 ms and 1300 ms and particularly preferably between 1000 ms and 1200 ms and particularly preferably 1100 ms. If the method according to at least one embodiment of the invention is performed on a magnetic resonance device with a main magnetic field with 1.5 T, then the inversion time is typically between 800 ms and 1000 ms and preferably between 900 ms and 950 ms. The high frequency pulse which is used to excite nuclear spins in the context of the gradient magnetic resonance sequence is, for example, between 2° and 20°, preferably between 5° and 15° and particularly preferably between 8° and 10°.

The recording area which is recorded by the eighth diagnostic scan Mb9 is a volume which is phase-coded in a first direction and in a second direction and frequency-coded in a third direction. The second direction is perpendicular to the first direction and the third direction is perpendicular to the first and to the second direction. The first direction and the second direction preferably define a sagittal layer orientation. The pixel resolution is preferably isotropic. A range of between 0.5 mm and 1.7 mm, preferably a range of between 0.8 mm and 1.4 mm and particularly preferably a range of between 1.0 mm and 1.2 mm has proved suitable as the pixel resolution in the first direction and/or in the second direction and/or in the third direction.

The recording area of the eighth diagnostic scan Mb9 is preferably a volume which has a spatial expansion in the range of between 150 mm and 300 mm, preferably between 200 mm and 240 mm and particularly preferably of 220 mm in the first direction and/or in the second direction. The spatial expansion in the first direction and in the second direction preferably correspond. The spatial expansion of the recording area in the third direction is in the range of between 150 mm and 250 mm, preferably between 180 mm and 220 mm and particularly preferably 200 mm. The second direction preferably connects an anterior and a posterior position of the head of the examination object. The first direction is preferably a lateral direction.

The number of voxels per measurement layer in the first direction is for example, between 128 and 256, preferably between 160 and 220 and particularly preferably 192. The number of voxels in the second direction preferably corresponds to the number of voxels in the first direction. Interpolation of the voxels or a zero-filling of the k-space take place so that the interpolated voxels are the same size in the first direction and in the second direction. The bandwidth of the frequency coding for the eighth diagnostic scan Mb9 is typically in the range of between 150 Hertz per pixel and 500 Hertz per pixel and preferably between 180 Hertz per pixel and 270 Hertz per pixel.

A period in the range of between 1000 ms and 6000 ms, preferably between 1500 ms and 3500 ms and particularly preferably between 2200 ms and 2400 ms is preferably selected as the repetition time. Preferably, the eighth diagnostic scan Mb9 takes place with an echo time which exceeds the minimum echo time by 20% maximum, preferably by 10% maximum, and particularly preferably does not exceed it at all. A period of less than 5 ms, preferably of less than 4 ms and particularly preferably of less than 3 ms is preferably selected as the echo time. Preferably, phase oversampling in the range of between 10% and 50%, in particular between 20% and 30% takes place in the first direction. Preferably, phase oversampling is omitted in the second direction.

Acceleration technology is preferably used to acquire the eighth diagnostic measurement data. In particular, the use of parallel imaging is conceivable which is preferably used with an acceleration factor of between 2 and 4, particularly preferably with an acceleration factor of 3. In particular, the use of Compressed Sensing acceleration technology is in turn conceivable.

The aforementioned parameters regarding the magnetic resonance sequence for the eighth diagnostic scan Mb9 are advantageously selected such that the eighth diagnostic measurement data can be recorded in full in less than 250 seconds, in particular in less than 200 seconds, advantageously in less than 185 seconds with the magnetic resonance sequence used. Eighth image data reconstructed from the eighth diagnostic measurement data can be reconstructed and provided for diagnosis immediately after completion of the eighth diagnostic scan Mb9.

The ninth measuring block Bb9 ends at the point in time Tb10. The tenth point in time Tb10 in the case shown is 615 s after the starting time Tb1 of the second head imaging. The tenth point in time Tb10 therefore represents the end of the acquisition of the measurement data and the end of the evaluation in the second head imaging shown. The tenth point in time Tb10 therefore ends the second head imaging.

The ninth measuring block Bb9, in particular the eighth diagnostic scan Mb9, is dependent on the receive unit and the strength of the main magnetic field of the magnetic resonance device. The specified ranges of the areas for parameters which are specified in the description of the ninth measuring block Bb9 for 3 Tesla and a receive unit with 32 reception channels are typically also applicable to other configurations. The aforementioned embodiment of the eighth diagnostic scan Mb9 is preferably used at 3 Tesla and with a receive unit with 32 or more reception channels. If fewer than 32 receive channels are used, the acceleration factor is preferably reduced, whereby the fifth period can be increased to 246 s.

If the eighth diagnostic scan Mb9 is performed with a magnetic resonance device with a main magnetic field with a strength of 1.5 Tesla, the following parameters are preferably changed:
the repetition time is preferably 2200 ms
the echo time is preferably between 235 ms
the acceleration factor is preferably
the resulting sixth period is typically between 210 s and 260 s, preferably between 230 s and 240 s.

Recording Parameter Ratio Between Diagnostic Scans

The magnetic resonance sequences used for the recordings Mb1-Mb9 have characteristic properties and/or characteristic dependencies which relate to different parameters. For example, sampling of the k-space for at least one, preferably for at least two, most preferably for at least three recordings takes place in a Cartesian manner wherein, for example, the recordings Mb1, Mb3, Mb7 can take place in a Cartesian manner. Such recordings typically have a particularly strong contrast. At least one, preferably at least two of the diagnostic scans Mb2-Mb9 take place three-dimensionally, wherein the resolution for three-dimensional recordings is preferably isotropic. Three-dimensional recordings can typically be recorded faster and/or with a higher signal-to-noise ratio compared to two-dimensional recordings. The in-plane resolution is preferably the same and/or in particular also independent of the layer orientation for two-dimensional diagnostic measurement data which has no diffusion weighting. As a result, the different diagnostic scans are particularly easily comparable.

If the spatial expansion in the second direction corresponds to the spatial expansion in the first direction for one of the diagnostic scans Mb2-Mb9, the second direction preferably connects an anterior and a posterior position of the head of the examination object. If the spatial expansion in the second direction corresponds to the spatial expansion in the first direction in a diagnostic scan of the diagnostic scans Mb2-Mb9, the diagnostic scan is typically based on a gradient echo magnetic resonance sequence, in particular on a FLASH and/or an EPI. This is advantageous as such a magnetic resonance sequence for recording diagnostic measurement data is designed to scan a layer in the k-space particularly rapidly, in particular after a single high frequency pulse used to excite nuclear spins. Through a quadratic expansion of a measurement layer, in other words, of a corresponding spatial expansion in the first direction and in the second direction, the efficiency of such a magnetic resonance sequence can be put to particularly good use in the recording of much measurement data and thus increase the signal-to-noise ratio of the resulting image data.

If the spatial expansion in the second direction is less than the spatial expansion in the first direction in one of the diagnostic scans Mb1-Mb9, then the second direction is preferably a lateral direction. Thereby, the special anatomy of the head can be used advantageously to reduce the corresponding period. In particular, this is advantageous for spin echo-based magnetic resonance sequences as a period for recording diagnostic measurement data is determined, in particular, by the number of voxels in the second direction and a reduction in the number of voxels in the second direction can result in a reduction in the corresponding period.

The resolution of the overview measurement data and/or the eighth diagnostic measurement data is preferably isotropic. Preferably, at least two of the recordings Mb1-Mb9 and/or at least one of the diagnostic scans Mb2-Mb9 takes place three-dimensionally. A layer thickness preferably corresponds to recordings of two-dimensional diagnostic measurement data which are recorded with the same layer orientation. Thereby the diagnostic measurement data which is recorded with the same layer orientation and same layer thickness is particularly easily comparable: such diagnostic image data displays the same sections of the area under examination in different contrasts, whereby a tissue and/or the anatomy and/or a pathology can be identified with particularly precision. The layer orientation of at least two two-dimensional recordings of the recordings Mb2-Mb9 of the diagnostic measurement data differs. This enables at least two different views of the area under examination, which views preferably also have a different contrast from each other.

Two-dimensional diagnostic measurement data which does not have diffusion weighting is preferably recorded with the same layer thickness, same distance between two adjacent measurement layers and/or same in-plane resolution. As a result, the diagnostic measurement data is particularly easily comparable. At least four, preferably at least five and particularly preferably at least six of the eight diagnostic scans Mb2-Mb9 have the same number of voxels per layer in at least one direction, in particular in the first direction. The spatial expansion in at least one direction, in particular in the first direction, preferably corresponds to at least five, in particular to at least six, preferably to at least seven of the eight diagnostic scans Mb2-Mb9. The number of voxels in one direction, in particular in the first direction, is preferably lower for the fifth diagnostic scan Mb6 and/or eighth diagnostic scan Mb9 than for at least one of the diagnostic scans Mb2, Mb3, Mb4, Mb5, Mb7, Mb8. By reducing the number of voxels, for example, the period which is necessary for the fifth diagnostic scan Mb6 can be reduced, which is efficient in particular for diffusion-weighted recording as it has corresponding magnetic resonance sequence modules for fat saturation and/or diffusion weighting. By reducing the number of voxels, for example, the period which is necessary for the eighth diagnostic scan Mb9 can be reduced, which is efficient in particular as it has corresponding magnetic resonance sequence modules for fat saturation. The number of voxels in one direction, in particular in the first direction, is preferably lower for the fifth diagnostic scan Mb6 than for the eighth diagnostic scan Mb9. This is particularly advantageous as for the fifth diagnostic scan Mb6 compared to the eighth diagnostic scan Mb9, it has a module for diffusion weighting which also increases the SAR load for the examination object and/or the sixth period.

The number of measurement layers for the sixth diagnostic scan Mb6 is preferably greater than for at least one of the two-dimensional diagnostic scans Mb2, Mb3, Mb4, Mb5, Mb7, Mb8. The distance between two adjacent measurement layers is preferably shorter for the fifth diagnostic scan Mb6 than for at least one of the diagnostic scans Mb2, Mb3, Mb4, Mb5, Mb7, Mb8. This is particularly advantageous as the diffusion-weighted fifth diagnostic scan Mb6 therefore has a continuous transition between adjacent layers compared to the diagnostic scans Mb2, Mb3, Mb4, Mb5, Mb7, Mb8, whereby an ADC card and/or a TRACE image can be determined with particular precision. The pixel resolution of the eighth diagnostic scan Mb9 in the third direction is preferably greater than for the recordings Mb1-Mb8. The spatial expansion of a pixel in the third direction is typically smaller for the eighth diagnostic scan Mb9 than for the recordings Mb1-Mb8. Thereby an isotropic pixel resolution can be achieved in a time-efficient manner for the eighth diagnostic scan Mb9.

Preferably, a T1-weighted recording Mb2 has a layer orientation which corresponds to the layer orientation of a three-dimensional diagnostic scan Mb9. Preferably, the diagnostic scans Mb2-Mb9 are recorded with at least two different layer orientations. This enables at least two different views of the area under examination and these views preferably also have different contrast from each other. Preferably, at least two diagnostic scans of the diagnostic scans Mb2-Mb9 take place respectively in one of the at least two different layer orientations. Thereby the variety of views and contrasts can be increased, enabling a more reliable diagnosis.

Preferably the diagnostic scans Mb2-Mb9 each have different contrasts from each other. Preferably, two of the diagnostic scans Mb2-Mb9 differ from each other solely in that they are recorded before and after the administration of contrast agent Cb. As a result, tissue and/or fluid, in which the contrast agent particularly accumulates, can be identified and/or extracted particularly well. Preferably, an accumulation of contrast agent in the head of the examination object is necessary for at least two of the diagnostic scans Mb2-Mb9, enabling a characteristic contrast to be achieved. As a result, a reliable diagnosis and/or a more reliable exclusion of a disease can be guaranteed. Preferably, at least one of the diagnostic scans Mb2-Mb9 has a T1 contrast, preferably at least one of the diagnostic scans Mb2-Mb9 has a T2 contrast, preferably at least one of the diagnostic scans Mb2-Mb9 has a FLAIR contrast, preferably at least one of the diagnostic scans Mb2-Mb9 has a susceptibility contrast, preferably at least one of the diagnostic scans Mb2-Mb9 has a GM-WM-T1 contrast in which the contrast between Gray Matter and White Matter is greater compared to the T1 contrast, and preferably at least one of the diagnostic scans Mb2-Mb9 has a diffusion-weighted contrast. Typically, the signal intensity depends on the underlying tissue and the contrast of the recording so that different tissue is displayed with different contrasts, whereby a tissue can be determined with particular precision and a pathology can thus be detected with particular precision. When the diagnostic measurement data is reconstructed as diagnostic image data, the diagnostic image data displays the contrast of the diagnostic measurement data. The aforementioned contrasts enable, in particular, a comprehensive diagnosis of different clinical pictures, in particular of the aforementioned diseases in the section "General information about the second head imaging".

At least two of the three-dimensional recordings Mb1, Mb9 have the same layer orientation which is defined by the first direction and the second direction. Preferably, at least two of the eight diagnostic scans Mb2-Mb9 are recorded by way of spin echo magnetic resonance sequences. The high frequency pulse which is used to refocus nuclear spins in the context of the spin echo magnetic resonance sequence is preferably less than 180°, in particular preferably less than 155°. The advantage of such a choice of high-frequency pulse for refocusing is that the SAR load on the patient which is caused by the high-frequency pulse for refocusing is reduced, whereby the overall SAR load on the patient can be reduced and/or the frequency of the high-frequency pulse for refocusing can be increased, whereby the period of the diagnostic scan can be reduced.

Preferably, at least five of the eight diagnostic scans Mb2-Mb9 are recorded by way of the gradient echo magnetic resonance sequences. Preferably, one of the five diagnostic scans Mb2-Mb9 is recorded by way of an EPI magnetic resonance sequence. Preferably, the measurement data recorded with an EPI magnetic resonance sequence are recorded with fat saturation. As, in particular, a module comprising a magnetic resonance sequence for fat saturation increases the period of a magnetic resonance sequence and/or the SAR load for the examination object, a combination of a module for fat saturation with a particularly fast magnetic resonance sequence such as, for example, an EPI-based magnetic resonance sequence, and/or with a magnetic resonance sequence with a particularly low number of high-frequency pulses and therefore with a particularly low SAR load for the examination object such as, for example, a gradient echo-based magnetic resonance sequence, is particularly advantageous.

Preferably, the measurement data recorded with an EPI magnetic resonance sequence is recorded with an echo time which preferably exceeds the minimum echo time by 20% maximum, preferably by 10% maximum, and particularly preferably does not exceed it at all. Preferably, phase oversampling is omitted with a recording with an EPI magnetic resonance sequence phase. Thereby the period of the corresponding measuring block and/or the first imaging period can be reduced.

The bandwidth of frequency coding for the fifth diagnostic scan Mb6 is typically greater than 1000 Hertz per pixel and preferably greater than 1200 Hertz per pixel. In particular, rapid scanning of the k-space, high signal intensity and/or a largely constant contrast can be guaranteed thereby for EPI-based magnetic resonance sequences during scanning. The lower signal-to-noise ratio resulting from the high bandwidth of frequency coding can be compensated by a higher number of recorded points in the k-space for such magnetic resonance sequences, whereby the function of the EPI-based magnetic resonance sequences can be utilized particularly well by the high bandwidth of frequency coding. In addition, artifacts, in particular due to movement, can be reduced. The bandwidth of frequency coding for the first and/or the third and/or the fourth and/or the seventh diagnostic scan Mb2, Mb4, Mb5, Mb8 is typically in the range of between 200 Hertz per pixel and 500 Hertz per pixel, preferably between 300 Hertz per pixel and 400 Hertz per pixel. In particular, for spin echo-based magnetic resonance sequences the signal-to-noise ratio can be improved by the choice of such a low bandwidth of frequency coding. The bandwidth of the frequency coding of at least two, in particular of at least three of the diagnostic scans Mb2, Mb4, Mb5, Mb8 preferably corresponds or differs by a maximum of 50 Hertz per pixel. The bandwidth of the frequency coding is typically less for the second and/or sixth and/or eighth diagnostic scan Mb3, Mb7, Mb9 than for the first and/or the third and/or the fourth and/or the seventh diagnostic scan Mb2, Mb4, Mb5, Mb8. These dependencies of the bandwidth of the frequency coding enable a particularly good signal-to-noise ratio of the diagnostic measurement data, or diagnostic image data, based on which a particularly reliable diagnosis can be made and/or a particularly short first imaging period which is within the aforementioned limits.

The repetition time of the overview scan Mb1 is preferably shorter than the repetition time of at least one diagnostic scan Mb2-Mb9. The repetition times of the T1-weighted recordings Mb2, Mb5 and Mb8 preferably correspond. The T1-weighted recordings Mb2, Mb5 and Mb8 preferably have the shortest repetition time of the diagnostic scans Mb2-Mb9. The second diagnostic scan Mb3 preferably has the longest repetition time of the diagnostic scans Mb2-Mb9. The repetition time of the sixth diagnostic scan Mb7 is preferably at least 20 times as long as the repetition time of the first diagnostic scan Mb2. The repetition time of the fifth diagnostic scan Mb6 is preferably at least 10 time as long as the repetition time of the first diagnostic scan Mb2. The repetition time of the eighth diagnostic scan Mb9 is preferably at least 5 times as long as the repetition time of the first diagnostic scan Mb2. The repetition time of the third diagnostic scan Mb4 is preferably at least twice as long as the repetition time of the first diagnostic scan Mb2. The repetition time of the second diagnostic scan Mb3 is preferably at least 30 times as long as the repetition time of the first diagnostic scan Mb2.

The echo time of the overview scan Mb1 is preferably shorter than the echo time of at least one diagnostic scan Mb2-Mb9. The echo times of the T1-weighted recordings Mb2, Mb5 and Mb8 preferably differ by 0.3 ms maximum. The T1-weighted recordings Mb2, Mb5 and Mb8 preferably have the shortest echo time of the diagnostic scans Mb2-Mb9. The second diagnostic scan Mb3 preferably has the longest echo time of the diagnostic scans Mb2-Mb9. The echo time of the sixth diagnostic scan Mb7 is preferably at least 25 times as long as the echo time of the first diagnostic scan Mb2. The echo time of the fifth diagnostic scan Mb6 is preferably at least 15 times as long as the echo time of the first diagnostic scan Mb2. The echo time of the eighth diagnostic scan Mb9 preferably differs by a maximum of 2 ms from the echo time of the first diagnostic scan Mb2. The echo time of the third diagnostic scan Mb4 is preferably at least five times as long as the echo time of the first diagnostic scan Mb2. The echo time of the second diagnostic scan Mb3 is preferably at least 40 times as long as the echo time of the first diagnostic scan Mb2.

These dependencies of the repetition times and/or echo times enable particularly advantageous contrasts of the diagnostic measurement data, or diagnostic image data, based on which a particularly reliable diagnosis can be made and/or a particularly short first imaging period which is within the aforementioned limits.

Temporal Sequence of the Diagnostic Scans

The second head imaging is characterized in that a maximum of one first user interaction Ib1 is required at the start of the first head imaging. The subsequent measuring blocks Bb2-Bb9 take place automatically, enabling the user to monitor the embodiment of the methods, for example. The temporal sequence of the measuring blocks Bb2-Bb5 before the administration of the contrast agent Cb can be selected as required. The temporal sequence of the measuring blocks Bb2-Bb5 is preferably selected such that the measurement data recorded by way of the measuring blocks Bb2-Bb5 and image data which can be reconstructed from it is in descending order of importance for the user. Thus, diagnostic measurement data of particular relevance for a diagnosis can be recorded at an earlier time at which the patient is more cooperative and/or the probability of the patient moving is lower, whereby the quality of the diagnostic measurement data can be increased. The sequence of the measuring blocks Bb2-Bb5 is preferably selected such that diagnostic scans with consistent orientation are summarized in one block and the at least two blocks are executed one after the other. This reduces the probability of the patient moving between two diagnostic scans of the same orientation, in other words, two diagnostic scans of the same block, whereby the two diagnostic scans of the same orientation can be better compared with each other and in particular can also be depicted superimposed and/or a subtraction can be performed. The sequence of the blocks and/or the sequence of the diagnostic scans in a block can be selected as required. It is thereby possible to individually adjust the sequence to the requirements of the user.

Specifically, in the second head imaging, contrast agent Cb is administered at least once. The administration of contrast agent Cb is chronologically arranged such that for the following diagnostic scans, in particular for the seventh diagnostic scan Mb8 and/or the eighth diagnostic scan Mb9 the most appropriate possible accumulation of the administered contrast agent is present in the head of the examination object. At the same time, the diagnostic scans in the second head imaging subsequent to the administration of contrast agent Cb are chronologically arranged particularly advantageously with regard to the accumulation of the administered contrast agent. The temporal sequence of the measuring blocks Bb6-Bb9 after administration of the contrast agent Cb is subject to particular criteria which, in particular, result from the sensitivity of individual diagnostic recordings in terms of the contrast agent used.

The measuring blocks Bb6-Bb9 to be arranged after the sixth point in time Tb6, the point in time at which contrast agent Cb is administered, can typically be divided into two groups. The first of the two groups comprises measuring blocks with diagnostic scans which are insensitive to the administered contrast agent Cb. The second of the two groups comprises measuring blocks with diagnostic scans which require the accumulation of a contrast agent.

Measuring blocks in the second group are advantageously performed at a point in time at which the contrast agent has been distributed in full in vessels of the area under examination. This point in time, in FIG. 2 the eighth point in time Tb8, is typically at least one minute, advantageously at least two minutes and particularly advantageously at least three minutes after the point in time Tb6 of the administration of contrast agent Cb. Highly advantageously, between 5 minutes and 15 minutes elapse between the administration of the contrast agent Cb and the starting point of the measuring blocks of the second group. A waiting period between the point in time Tb6 of the administration of contrast agent Cb and the start of the measuring blocks of the second group Tb8 is preferably used for measuring blocks of the first group. Preferably, the waiting time is completely occupied by measuring blocks, wherein the measuring blocks are preferably consecutive and/or the period of such a measuring block is included in full in the pure measurement period of the corresponding diagnostic scan. As a result, the second imaging period which is required for the entire second head imaging can be reduced and efficient use made of the waiting period.

The temporal sequence of the measuring blocks in the second group, in particular of the measuring blocks Bb8, Bb9, after administration of the contrast agent Cb can be selected as required. The temporal sequence of the measuring blocks of the second group is preferably selected according to their need for intensity and/or homogeneity in the accumulation of the contrast agent. The temporal sequence of the measuring blocks of the second group can be selected such that the measurement data recorded by way of the measuring blocks of the second group and image data which can be reconstructed from it is in descending order of importance for the user. The temporal sequence of the measuring blocks of the second group can be selected such that diagnostic scans with corresponding orientation are performed in direct succession.

The measuring blocks of the second group preferably produce diagnostic measurement data which can be reconstructed as image data which has a contrast which is influenced by the administration of contrast agent Cb. The seventh diagnostic scan Mb8 and the fourth diagnostic scan Mb5 preferably differ only through the administration of contrast agent Cb which takes place between the two measuring blocks Bb5 and Bb8. The period between the two measuring blocks Bb5 and Bb8 is preferably selected such that the contrast agent can on the one hand disperse in vessels of the area under examination in full and on the other hand, minimally so that the probability of a movement between the two measuring blocks Bb5 and Bb8 is minimized. The measuring block Bb5 is preferably performed last before the administration of the contrast agent Cb. Thereby vessels and/or tissue which are affected by an accumulation of the contrast agent can be particularly easily identified.

Particularly advantageously, a T1 contrast is selected for the fourth diagnostic scan Mb5 and for the seventh diagnostic scan Mb8. For a T1 contrast without contrast agent enrichment, a fluid appears dark in the corresponding image data reconstructed from the fourth diagnostic measurement data. For a T1 contrast after contrast agent enrichment, a fluid appears light in the corresponding image data reconstructed from the seventh diagnostic measurement data. As a result, when using a T1 contrast for the fourth diagnostic scan Mb5 and for the seventh diagnostic scan Mb8, vessels with fluids can be depicted particularly easily. Likewise, a recording corresponding to the eighth diagnostic scan Mb9 can be performed before the time at which the contrast agent Cb is administered so that the influence of the contrast agent on the eighth diagnostic scan Mb9 can be determined.

Recordings which are insensitive to the administered contrast agent Cb typically acquire insensitive measurement data which can only be slightly altered by the presence of a contrast agent or not at all. In particular, insensitive measurement data reconstructed as image data is not influenced by the administration of contrast agent Cb. The fifth and the sixth diagnostic scan Mb6, Mb7 and therefore also the sixth and the seventh measuring block are preferably insensitive. Here any detrimental influence of the contrast agent administered to the examination object on the fifth and sixth diagnostic measurement data is accepted in order to be able to keep the second imaging period as short as possible. Insensitive measuring blocks are preferably performed immediately after the administration of contrast agent Cb. Preferably, all recordings included in the second head imaging are performed in the period between the point in time Tb6 of the administration of contrast agent Cb and the start of the recordings of the second group Tb8. The second imaging period can be minimized thereby.

The temporal sequence of the measuring blocks in the first group, in particular of the measuring blocks Bb6, Bb1 after administration of the contrast agent Cb can be selected as required. The temporal sequence of the measuring blocks of the first group is preferably selected such that the measurement data recorded via the measuring blocks of the first group and image data which can be reconstructed from it is in descending order of importance for the user. The temporal sequence of the measuring blocks of the first group is preferably selected such that diagnostic scans with corresponding orientation are performed in direct succession.

The waiting period between the administration of contrast agent Cb and the seventh and eighth diagnostic scans Mb8, Mb9 can be put to particularly good use by the appropriate temporal arrangement of the fifth and sixth diagnostic scans Mb6, Mb7. In this way, it is possible to ensure that the maximum imaging period can be observed for the second head imaging. For the second head imaging with the administration of contrast agent Cb, the measuring blocks after the administration of contrast agent Cb have a total period which is longer than the total period of the measuring blocks before the administration of contrast agent Cb. The total period of the measuring blocks of the second group is preferably less than the total period of the measuring blocks before the administration of contrast agent Cb. Preferably, all the insensitive measuring blocks of the second head imaging are assigned to the first group so that the total period of the measuring blocks of the first group is maximized. Thereby the measuring blocks of the second group can start at as late as possible a time when the contrast agent has accumulated homogenously in the tissues and/or vessels concerned.

Ratio of the Period Between the Diagnostic Scans and the Overview Scan

The period of the ninth measuring block Bb9 is typically longer than the period of the third measuring block Bb3. The period of the third measuring block Bb3 is typically longer than the period of the sixth measuring block Bb6. The period of the sixth measuring block Bb6 is typically longer than the period of the fourth measuring block Bb4. The period of the fourth measuring block Bb4 is typically longer than the period of the seventh measuring block Bb7. The period of the seventh measuring block Bb7 is typically longer than the period of the second measuring block Bb2. The period of the second measuring block Bb2 is typically longer than the period of the fifth measuring block Bb5. The period of the fifth measuring block Bb5 typically corresponds to the period of the eighth measuring block Bb8. The period of the fifth measuring block Bb5 and/or the period of the eighth measuring block Bb8 is typically longer than the period of the first measuring block Bb1.

The period of the first measuring block Bb1 and of the second measuring block Bb2 together is preferably shorter than the period of the fourth measuring block Bb4. The period of the first measuring block Bb1 and of the fourth measuring block Bb4 together is preferably shorter than the period of the third measuring block Bb3. The period of the second measuring block Bb2 and of the fifth measuring block Bb5 together is preferably shorter than the period of the sixth measuring block Bb6. The period of the fourth measuring block Bb4 and of the fifth measuring block Bb5 together is preferably longer than the period of the third measuring block Bb3. The period of the fourth measuring block Bb4 and of the fifth measuring block Bb5 together is preferably longer than the period of the third measuring block Bb3. The period of the second measuring block Bb2 and of the fifth measuring block Bb5 together is preferably longer than the period of the seventh measuring block Bb7. The period of the third measuring block Bb3 and of the sixth measuring block Bb6 together is preferably shorter than the period of the ninth measuring block Bb9. The period of the first measuring block Bb1 and of the third measuring block Bb3 and of the sixth measuring block Bb6 together is preferably longer than the period of the ninth measuring block Bb9. The period of the second measuring block Bb2 and of the seventh measuring block Bb7 together is preferably longer than the period of the third measuring block Bb3. The period of the fifth measuring block Bb5 and of the eighth measuring block Bb8 together is preferably longer than the period of the seventh measuring block Bb7. The period of the fifth measuring block Bb5 and of the eighth measuring block Bb8 together is preferably shorter than the period of the fourth measuring block Bb4. The period of the first measuring block Bb1 and of the fifth measuring block Bb5 together is preferably longer than the period of the second measuring block Bb2. The period of the seventh measuring block Bb7 and of the sixth measuring block Bb6 together is preferably shorter than the period of the ninth measuring block Bb9. The period of the second measuring block Bb2 and of the fifth measuring block Bb5 and of the seventh measuring block Bb7 and of the eighth measuring block Bb8 together is preferably shorter than the period of the ninth measuring block Bb9.

The two measuring blocks comprising two-dimensional recordings which have the longest period are preferably arranged such that the recording of the corresponding measurement data takes place with fat saturation. This is particularly advantageous as a magnetic resonance sequence with a module for fat saturation typically has a longer period than a magnetic resonance sequence without a module for fat saturation. The fifth diagnostic scan Mb6 which has diffusion weighting typically requires at least one module for fat saturation and one module for diffusion weighting, whereby on account of these at least two modules, the sixth period Tb6 is typically longer than a period of a measuring block which has one or none of the modules and is based on the same magnetic resonance sequence as the fifth diagnostic scan Mb6. Nevertheless, in order to keep the sixth period Tb6 as short as possible, the fifth diagnostic scan Mb6 is performed with an EPI-based magnetic resonance sequence.

The period of reconstruction of the overview measurement data is typically 20% maximum, preferably 10% maximum and particularly preferably 5% maximum of the period of the recording of the overview measurement data Mb1. The period of the reconstruction diagnostic measurement data is typically at least 1 s and/or 10% maximum, preferably 5% maximum and particularly preferably 3% maximum of the period of the recording of the diagnostic measurement data Mb2-Mb9.

General Remarks Concerning FIG. 1 and FIG. 2

The measurement data recorded in a measuring block Ba, Bb is preferably reconstructed as image data and made available to the user on the display unit and/or stored in a database. The measurement data can also be stored in a database. In order to be able to record meaningful diagnostic measurement data in the maximum specified imaging period, different acceleration technologies and/or automation techniques are used for the presented procedures for head imaging. Hereinafter some of the acceleration technologies and automation techniques used for head imaging are presented. The presented techniques can be used individually as well as combined. Some techniques presented can be applied to both the first head imaging and the second head imaging.

Reduction of User Interactions

A maximum of one user interaction takes place during the head imaging shown in FIG. 1. A maximum of two user interactions preferably take place and particularly advantageously only one user interaction takes place during the head imaging shown in FIG. 2. The number of diagnostic scans during head imaging is in particular greater and particularly advantageously at least five times as great as the number of user interactions during head imaging. Furthermore, during head imaging at least the same number of automatic evaluation steps as user interactions takes place advantageously.

The number of user interactions is advantageously reduced by appropriate automation measures during head imaging. Measurement parameters such as, for example, layer positioning and/or shim volume can be automatically copied between different measuring blocks. Voice commands can also be issued automatically to the examination object, for example, for the administration of contrast agent and/or the administration of the contrast agent itself can take place automatically so that the user does not have to concentrate on it during the performance of head imaging. At the same time, the protocol used for head imaging can be dynamically adjusted to patient-specific features. Thus, a recording area for the diagnostic measurement data can be automatically ascertained on the basis of a patient value and/or by way of the overview measurement data.

At the same time, it is advantageous that at the points in head imaging at which a user interaction Ia, Ib is required, the user is advantageously given an instruction for the respective user interaction directly on the display unit. Advantageously, proposals are already submitted to the user automatically and it only remains for him to accept or amend them. At the same time, for a necessary user interaction directly appropriate tools are advantageously displayed to the user for the performance of the user interaction. In such a way, the user can be led through the workflow during head imaging. The time required for the user interaction can be reduced by way of the user guidance for the user interaction. The usual time for the user interaction Ia, Ib may in this way be half a minute maximum, advantageously 20 seconds maximum, particularly advantageously 10 seconds maximum and most advantageously 5 seconds maximum.

Overall, the renunciation by and large of user interactions compared to traditional examinations of the head which advantageously only take place at the start of head imaging makes it possible to accelerate the sequence of head imaging such that the acquisition of diagnostic measurement data required for the assessment of the head of the examination object in the maximum imaging period is enabled. The evaluation of the overview measurement data in the evaluation step Ea1, Eb1 also takes place automatically particularly advantageously.

The reduction of the number of necessary user interactions can result in a reduced requisite imaging period for head imaging. The operation of head imaging is also particularly user-friendly as a result. The results of head imaging can be particularly robust as they are less susceptible to user errors. The intelligent ranking of the user interactions in the sequence of head imaging can therefore improve the technical reliability of the sequence of head imaging. At the same time, diagnostic measurement data standardized in this way can be acquired in head imaging. An imaging period for head imaging is also standardized and can therefore be well predicted. This can lead to improved planning of the utilization of the magnetic resonance device.

The use of acceleration technology such as, for example, parallel imaging, partial Fourier technique and/or Compressed Sensing can enable a recording of the diagnostic measurement data in a particularly short recording time.

Particularly in a comprehensive diagnosis of the head, the employment of acceleration technology can be particularly useful due to the large amount of recording time usually required. Thus, in particular, a condition which is temporary on account of the administration of contrast agent can also be recorded efficiently and quickly. In addition, the influence of the movement of the examination object on the diagnostic magnetic resonance measurement data can be significantly reduced. The use of an acceleration technology can also enable the robust acquisition of diagnostic magnetic resonance measurement data in the case of an uncooperative patient or children.

Figure 3:
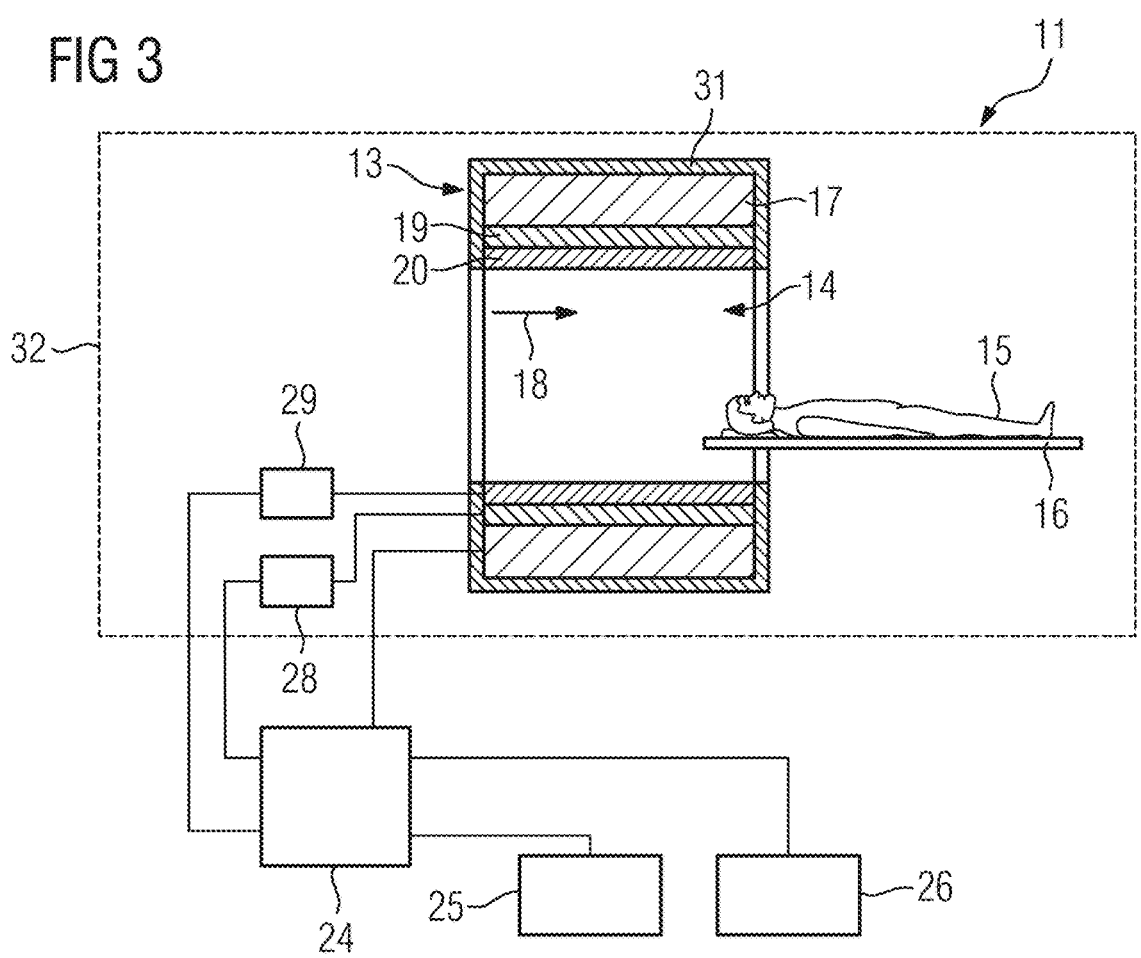
FIG. 3 illustrates a magnetic resonance device for the performance of head imagings according to an example embodiment.

FIG. 3—a Magnetic Resonance Device

FIG. 3 shows a diagrammatic view of a magnetic resonance device 11 according to at least one embodiment of the invention for the performance of head imaging in accordance with FIG. 1-FIG. 2. The magnetic resonance device 11 comprises a detector unit formed by a magnet unit 13 with a main magnet 17 for the generation of a strong and particularly constant main magnetic field 18. In addition, the magnetic resonance device 11 has a cylindrical patient receiving area 14 for receiving an examination object 15, in the present case a patient, wherein the patient receiving area 14 is cylindrically enclosed in one peripheral direction of the magnet unit 13. The patient 15 can be pushed into the patient receiving area 14 via the patient positioning device 16 of the magnetic resonance device 11. The patient positioning device 16 has a couch for this purpose which can be moved inside the magnetic resonance device 11. The magnet unit 13 is shielded to the outside via the housing cover 31 of the magnetic resonance device.

Furthermore, the magnet unit 13 has a gradient coil unit 19 for the production of magnetic field gradients which is used for spatial encoding during imaging. The gradient coil unit 19 is controlled via a gradient control unit 28. In addition, the magnet unit 13 has a high-frequency antenna unit 20 which in the case shown is designed as a body coil permanently integrated into the magnetic resonance device 11, and a high-frequency antenna control unit 29 for exciting polarization which sets itself in the main magnetic field 18 produced by the main magnet 17. The high-frequency antenna unit 20 is controlled by the high-frequency antenna control unit 29 and radiates high frequency magnetic resonance sequences into an area under examination essentially formed by the patient receiving area 14. Furthermore, the high-frequency antenna unit 20 is designed to receive magnetic resonance signals, in particular from the patient 15.

The magnetic resonance device 11 has a computing unit 24 to control the main magnet 17, the gradient control unit 28 and the high-frequency antenna control unit 29. The computing unit 24 controls the magnetic resonance device 11 centrally, for example, the performance of a predetermined imaging gradient echo sequence. Control information such as, for example, imaging parameters and reconstructed magnetic resonance images can be made available to a user on a display unit 25 of the magnetic resonance device 11. In addition, the magnetic resonance device 11 has an input unit 26 by way of which information and/or parameters can be input by a user during a measurement procedure. The computing unit 24 may comprise the gradient control unit 28 and/or the high-frequency antenna control unit 29 and/or the display unit 25 and/or the input unit 26.

Furthermore, the magnetic resonance device 11 comprises a measurement data acquisition unit 32. The measurement data acquisition unit 32 in the present case is formed by the magnet unit 13 together with the high-frequency antenna control unit 29 and the gradient control unit 28. The magnetic resonance device 11 together with the measurement data acquisition unit 32 and the computing unit 24 is therefore designed for performing a method according to at least one embodiment of the invention.

The magnetic resonance device 11 shown may, of course, include other components usually found in magnetic resonance devices 11. In addition, a general function of a magnetic resonance device 11 is known to a person skilled in the art so that there is no need for a detailed description of the other components.

Figure 4:
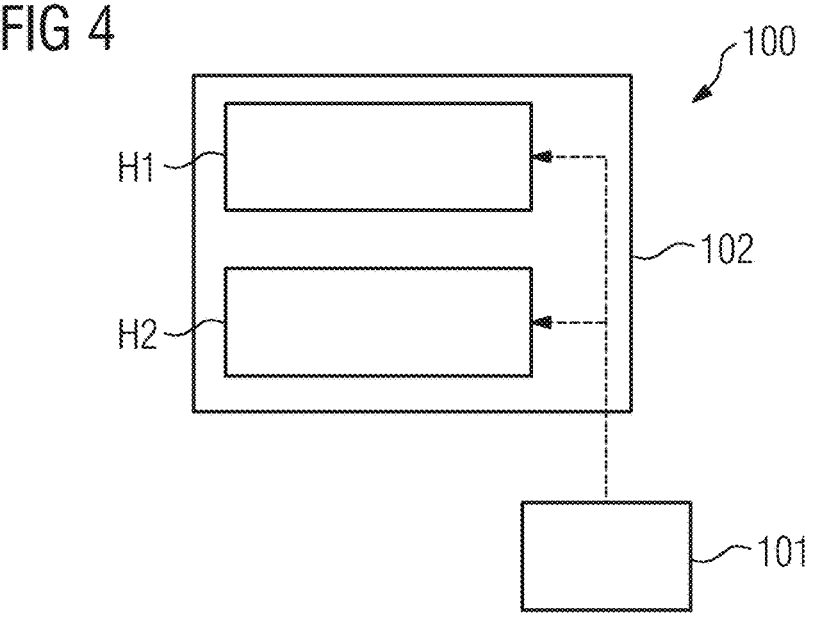
FIG. 4 illustrates a selection system which enables a user to select a head imaging to be performed according to an example embodiment.

FIG. 4—the Selection System

FIG. 4 shows a selection system 100 which enables a user to select the head imaging to be performed. The selection system 100 comprises a user interface via which the user can select the head imaging to be performed. For this the user interface comprises a sample unit 101 and an output unit 102. The sample unit can, in particular, be designed as an input unit 26 of the magnetic resonance device in accordance with FIG. 3. The output unit 102 can, in particular, be designed as a display unit 25 of the magnetic resonance device 11 in accordance with FIG. 4. In certain cases, it is also conceivable that the selection system 100 shown in FIG. 4 is separate from the magnetic resonance device 11.

The various head imaging choices for selection are shown on the output unit 102, in particular together with or on a suitable button H1, H2. In the case shown in FIG. 4, the first head imaging which is described in FIG. 1 is assigned to a first button H1 of the output unit 102, and the second head imaging which is described in FIG. 2 is assigned to a second button H2 of the output unit 102.

The depiction of the buttons H1, H2 and the associated inscription can be designed in a manner deemed appropriate to a person skilled in the art. The buttons H1, H2 can, for example, be inscribed with the diagnostic options of the respectively assigned head imaging. Thus, for example, the first button H1 can be inscribed such that the associated first head imaging is designed for the assessment of the anatomy and/or pathology of the head of the examination object. The second button H2 can be inscribed such that the associated second head imaging is designed for the assessment of a vascular disease and any neoplasm of the examination object. Furthermore, the maximum imaging period of the assigned head imaging can be displayed on the buttons H1, H2 respectively.

With the sample unit 101, the user can thus select a button H1, H2 in order to select the associated head imaging to be performed. In this way, the user can select the first head imaging to be performed by activating the first button H1 and the second head imaging to be performed by activating the second button H2. The selection of the button can be made by way of a method deemed appropriate by a person skilled in the art, for example, via a click, a double click, a drag & drop action, etc.

Naturally, other imaging procedures can also be displayed on the output unit 102, possibly also from other areas of the body of the examination object, and made available to the user for selection. The buttons H1, H2 can be arranged in a larger log tree which comprises other imaging procedures for selection.

After selection of a button H1, H2 by the user via the sample unit 101, the associated head imaging can be started. In this way, information about the selection of the button H1, H2 can be transferred from the selection system 100 to the magnetic resonance device 11. The selection of the button H1, H2 can immediately trigger the start of the associated head imaging. Advantageously, however, the entry of patient-specific features for respective head imaging is first made possible for the user before head imaging starts.

Naturally it is also conceivable that at least one additional diagnostic scan is introduced into the presented head imaging. This can result in an extension of the imaging period of the respective head imaging. The possible additional at least one diagnostic scan may, for example, comprise functional head imaging.

Although the invention was illustrated and described in detail by the preferred exemplary embodiments, nevertheless the invention is not restricted by the examples disclosed and other variations can be derived by a person skilled in the art, without departing from the scope of the invention.

The invention claimed is:

1. A method for recording diagnostic measurement data of a head of an examination object in head imaging via a magnetic resonance device, the method comprising:
    performing an overview scan of the head of the examination object, the performing the overview scan including acquiring overview measurement data; and
    performing various diagnostic scans of the head of the examination object based on the acquired overview measurement data, the performing the various diagnostic scans including acquiring diagnostic measurement data,
    wherein the head imaging includes administering a contrast agent and the various diagnostic scans include a first diagnostic scan, a second diagnostic scan, a third diagnostic scan, a fourth diagnostic scan, a fifth diagnostic scan, a sixth diagnostic scan, a seventh diagnostic scan, and an eighth diagnostic scan,
    and wherein of the various diagnostic scans, the first diagnostic scan, the fourth diagnostic scan, the seventh diagnostic scan, and the eighth diagnostic scan have a T1 contrast,
    the second diagnostic scan has a T2 contrast with cerebrospinal fluid suppression and a longest repetition time of the various diagnostic scans,
    the third diagnostic scan has a susceptibility-weighted contrast,
    the fifth diagnostic scan has a diffusion-weighted contrast, and
    the sixth diagnostic scan has a T2 contrast.

2. The method as claimed in claim 1,
    wherein the diagnostic measurement data from the first diagnostic scan is acquired using a gradient echo magnetic resonance sequence, the gradient echo magnetic resonance sequence including a Fast Low-Angle Shot (FLASH' magnetic resonance sequence.

3. The method as claimed in claim 1,
    wherein the diagnostic measurement data from the fourth diagnostic scan is recorded in full in less than 50 seconds.

4. The method as claimed in claim 1,
    wherein the seventh diagnostic scan and the fourth diagnostic scan are based on a same diagnostic scan protocol,
    the fourth diagnostic scan is performed before administration of the contrast agent to the examination object, and
    the seventh diagnostic scan is performed after administration of the contrast agent to the examination object.

5. The method as claimed in claim 1,
    wherein the eighth diagnostic scan is acquired using a three dimensional gradient echo magnetic resonance sequence with preparation of magnetization with inversion recovery.

6. The method as claimed in claim 1,
    wherein a first contrast between Gray Matter and White Matter in the eighth diagnostic scan is greater than a second contrast between Gray Mater and White Matter in the first diagnostic scan.

7. The method as claimed in claim 1,
    wherein the first diagnostic scan, the second diagnostic scan, the third diagnostic scan, and the fourth diagnostic scan are performed before administration of the contrast agent.

8. The method as claimed in claim 1,
    wherein at least two diagnostic scans of the various diagnostic scans have a different orientation.

9. The method as claimed in claim 1,
    wherein at least two diagnostic scans of the various diagnostic scans are recorded based on spin echo magnetic resonance sequences.

10. The method as claimed in claim 1,
    wherein at least five diagnostic scans of the various diagnostic scans are recorded based on gradient echo magnetic resonance sequences.

11. The method as claimed in claim 10,
    wherein at least one diagnostic scan of the at least five diagnostic scans is recorded based on an EPI magnetic resonance sequence.

12. The method as claimed in claim 1,
    wherein a bandwidth of frequency coding for the fifth diagnostic scan is greater than 1000 Hertz per pixel.

13. The method as claimed in claim 1,
    wherein an echo time of the first diagnostic scan differs from an echo time of the fourth diagnostic scan by a maximum of 0.3 ms,
    the echo time of the first diagnostic scan differs from an echo time of the seventh diagnostic scan by a maximum of 0.3 ms, and
    the echo time of the fourth diagnostic scan differs from the echo time of the seventh diagnostic scan by a maximum of 0.3 ms.

14. The method as claimed in claim 1,
wherein at least two diagnostic scans of the various diagnostic scans are recorded two-dimensionally and with fat saturation.

15. The method as claimed in claim 1,
wherein at least four diagnostic scans of the various diagnostic scans have a same number of voxels per layer in at least one direction.

16. A magnetic resonance device comprising:
a measurement data acquisition unit; and
a computing unit, wherein
the magnetic resonance device is configured to perform the method of claim 1 by using the computing unit to control the measurement data acquisition unit.

17. A non-transitory computer readable medium including computer-readable instructions which, when executed by at least one processor, cause the at least one processor to perform the method of claim 1.

18. A method for recording diagnostic measurement data of a head of an examination object in head imaging via a magnetic resonance device, the method comprising:
performing an overview scan of the head of the examination object, the performing the overview scan including acquiring overview measurement data; and
performing various diagnostic scans of the head of the examination object based on the acquired overview measurement data, the performing the various diagnostic scans including acquiring diagnostic measurement data,
wherein the head imaging includes administering a contrast agent and the various diagnostic scans include a first diagnostic scan, a second diagnostic scan, a third diagnostic scan, a fourth diagnostic scan, a fifth diagnostic scan, a sixth diagnostic scan, a seventh diagnostic scan, and an eighth diagnostic scan,
and wherein of the various diagnostic scans, the first diagnostic scan, the fourth diagnostic scan, the seventh diagnostic scan, and the eighth diagnostic scan have a T1 contrast,
the second diagnostic scan has a T2 contrast with cerebrospinal fluid suppression,
the third diagnostic scan has a susceptibility-weighted contrast,
the fifth diagnostic scan has a diffusion-weighted contrast, and
the sixth diagnostic scan has a T2 contrast,
wherein a repetition time of the sixth diagnostic scan is at least 20 times as long as a repetition time of the first diagnostic scan.

19. A method for recording diagnostic measurement data of a head of an examination object in head imaging via a magnetic resonance device, the method comprising:
performing an overview scan of the head of the examination object, the performing the overview scan including acquiring overview measurement data; and
performing various diagnostic scans of the head of the examination object based on the acquired overview measurement data, the performing the various diagnostic scans including acquiring diagnostic measurement data,
wherein the head imaging includes administering a contrast agent and the various diagnostic scans include a first diagnostic scan, a second diagnostic scan, a third diagnostic scan, a fourth diagnostic scan, a fifth diagnostic scan, a sixth diagnostic scan, a seventh diagnostic scan, and an eighth diagnostic scan,
and wherein of the various diagnostic scans, the first diagnostic scan, the fourth diagnostic scan, the seventh diagnostic scan, and the eighth diagnostic scan have a T1 contrast,
the second diagnostic scan has a T2 contrast with cerebrospinal fluid suppression,
the third diagnostic scan has a susceptibility-weighted contrast,
the fifth diagnostic scan has a diffusion-weighted contrast, and
the sixth diagnostic scan has a T2 contrast,
wherein at least one diagnostic scan of the various diagnostic scans takes place three-dimensionally with a layer thickness in a layer orientation, and
at least another diagnostic scan of the various diagnostic scans takes place two-dimensionally with a same layer orientation and corresponding layer thickness as the at least one diagnostic scan.

* * * * *